US008969249B2

(12) United States Patent
Abrams et al.

(10) Patent No.: US 8,969,249 B2
(45) Date of Patent: Mar. 3, 2015

(54) SYNTHESIS AND BIOLOGICAL ACTIVITY OF BICYCLIC ABA ANALOGS

(75) Inventors: Suzanne Abrams, Saskatoon (CA); Adrian J. Cutler, Saskatoon (CA); Patricia Rose, Wilmington, DE (US); James Nyangulu, Antigonish (CA); Ken M. Nelson, Warman (CA)

(73) Assignee: National Research Council of Canada, Ottawa, Ontario ( * ) Notice: Subject to any disclaimer, the term of this patent is extended or adjusted under 35 U.S.C. 154(b) by 2073 days.

(21) Appl. No.: 11/596,297

(22) PCT Filed: May 10, 2005

(86) PCT No.: PCT/CA2005/000712
§ 371 (c)(1),
(2), (4) Date: Dec. 21, 2007

(87) PCT Pub. No.: WO2005/108345
PCT Pub. Date: Nov. 17, 2005

(65) Prior Publication Data
US 2008/0200339 A1 Aug. 21, 2008

Related U.S. Application Data

(60) Provisional application No. 60/569,775, filed on May 10, 2004.

(51) Int. Cl.
*A01N 37/00* (2006.01)
*A01N 37/10* (2006.01)
*C07C 63/36* (2006.01)
*C07C 69/738* (2006.01)
*A01N 31/08* (2006.01)
*A01N 35/04* (2006.01)
*A01N 35/06* (2006.01)
*A01N 37/06* (2006.01)
*A01N 37/42* (2006.01)
*C07C 59/90* (2006.01)

(52) U.S. Cl.
CPC .............. *C07C 69/738* (2013.01); *A01N 31/08* (2013.01); *A01N 35/04* (2013.01); *A01N 35/06* (2013.01); *A01N 37/06* (2013.01); *A01N 37/42* (2013.01); *C07B 2200/07* (2013.01); *C07C 59/90* (2013.01); *C07C 2102/10* (2013.01)
USPC ........... 504/313; 504/320; 560/126; 560/134; 562/490; 562/508

(58) Field of Classification Search
USPC .................. 504/313, 320, 321; 560/126, 134; 562/508, 490
See application file for complete search history.

(56) References Cited
PUBLICATIONS

Irvine, N., Anthracenone ABA Analogue as a Potenial Photoaffinity Reagent for ABA-binding Proteins, 2000, Phytochemistry, vol. 53, Issue 3, pp. 349-355.*
Metabolite Definition, 2000, Hawley's Condensed Chemical Dictionary, 14th Edition, 1 page.*
Todoroki, Y., Conformational Analysis of the Cyclohexenone Ring in Abscisic Acid and its Analogs with a Fused Cyclopropyl Ring, 2000, Tetrahedron, vol. 56, pp. 8095-8100.*
Blake, T., Effects of Abscisic Acid and its Acetylenic Alcohol on Dormancy Root Development and Transpiration in Three Conifer Species, 1990, Physiologia Plantarum, vol. 80, pp. 371-378.*
Nyangulu, J., An Affinity Probe for Isolation of Abscisic Acid-Binding Proteins, 2005, Journal of American Chemical Society, vol. 127, No. 6, pp. 1662-1664.*
International Preliminary Report on Patentability on PCT/CA2005/000712 dated Nov. 23, 2006.
Irvine N. M., Rose P. A., Cutler A. J., Squires T. M. and Abrams S. R., Phytochemistry, 53, 349 (2000).
Nyangulu et al. Org. Biomol. Chem., 2006, 4, 1400-1412.
Office Action dated Oct. 25, 2011 on Canadian patent application CA 2,566,455.

* cited by examiner

*Primary Examiner* — Johann R Richter
*Assistant Examiner* — Andriae M Holt
(74) *Attorney, Agent, or Firm* — Laura Catherine Eckenswiller

(57) ABSTRACT

Bicyclic abscisic acid (ABA) analogs of Formula (I) and (II) and the process for their production are disclosed. The bicyclic ABA analogs include the structural elements and functional groups of the parent molecule that are required for activity, and have an aromatic ring fused to the ring replacing the vinyl methyl group of absicisie acid. Methods for using the bicyclic ABA analogs to inhibit cell growth and seed germination are also disclosed.

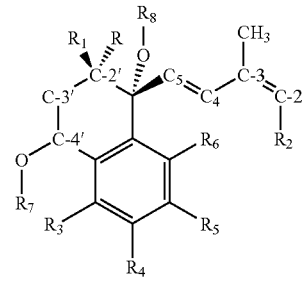

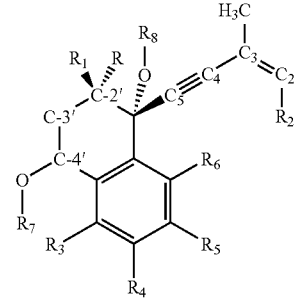

21 Claims, 7 Drawing Sheets

SYNTHESIS AND BIOLOGICAL ACTIVITY OF BICYCLIC ABA ANALOGS

PRIORITY CLAIM

This application claims the benefit of the filing date of U.S. Provisional Patent Application Ser. No. 60/569,775, filed May 10, 2004, for "SYNTHESIS AND BIOLOGICAL ACTIVITY OR NOVEL BICYCLIC ABA ANALOGS."

TECHNICAL FIELD

The invention relates generally to biotechnology, and more specifically to methods for synthesizing compositions for modulating plant seed germination and plant growth. The invention further relates to using modifications of the synthesized compositions to determine additional pathways through which abscisic acid (ABA) is metabolized.

BACKGROUND

The plant hormone abscisic acid [1] (FIG. 1) regulates many aspects of plant growth and development as well as responses to environmental stress (1). As used herein, brackets [ ] will be used to refer to chemical structures present in the attached FIGS. For example, in seed development, ABA induces synthesis of storage products, prevents germination of immature embryos and is involved in desiccation tolerance and germination of mature seed (1, 2). ABA levels in plants rise transiently in response to environmental stress and trigger a set of responses including rapid closure of the stomata reducing transpiration (1, 2). Numerous studies have been conducted to probe the structural requirements of ABA responses to develop analogs that are effective plant growth regulators (3, 4, 5). Some features of the ABA molecule [1], as shown in FIG. 1, appear to be required for activity, particularly the carboxyl and ketone groups, the six-member ring, the 7'-methyl group, and the cis double bond of the side chain. Other parts of the molecule can be modified without loss of activity. The ring double bond, both the 8'- and 9'-methyl groups, and the trans double bond of the side chain each can be altered and the resultant analog retains activity.

As shown in Scheme 1 (FIG. 1), ABA is catabolized predominantly through hydroxylation of the ring methyl groups or alternatively by conjugation to the glucose ester [7] (5, 6, 7, 8). The principal pathway of oxidation is through P450 monooxygenase mediated hydroxylation of the 8'-methyl group affording 8'-hydroxy ABA 2 which can rearrange to the closed form phaseic acid [3] (6). Alternative pathways, through hydroxylation of the 7'-methyl group affording 7'-hydroxy ABA [4] and the 9'-methyl group to give 9'-hydroxy ABA [5], which can also rearrange to the closed form neophaseic acid [6], have also been observed and contribute to ABA catabolism (7, 8). This catabolism by plant enzymes limits the practical application of ABA itself as a plant growth regulator (5). Metabolism resistant analogs of ABA altered at the 8' carbon atom have proved to be more persistent and more active than ABA (5).

DISCLOSURE OF INVENTION

In one embodiment, the invention discloses a variety of methods for forming bicyclic ABA analogs. In one embodiment, the planar vinyl methyl portion of ABA [1] (FIG. 1) has been replaced with an aromatic ring. Features of the ABA molecule are maintained, with preservation of the ABA side chain and the C-4' ketone group, with the additional planar ring linking the C-3' and C-7'-carbon atoms of ABA replacing the planar vinyl methyl group.

In an additional embodiment, the C-9' and/or C-10' (see FIG. 2 compound [8]) methyl group has been hydroxylated.

In a further embodiment, a process for producing bicyclic ABA and analogs is described. Racemic bicyclic methyl abscisate was synthesized from commercially available 1-tetralone. Geminal methyl groups were introduced adjacent to the carbonyl to give the dimethyl tetralone. The dimethyl tetralone was alkylated to give an allylic alcohol. The triple bond was reduced. The allylic alcohol was oxidized to an aldehyde, and then further oxidized to an ester. A ketone was introduced at the C-4' carbon (using the same carbon numbers as shown in FIG. 2 compound [8]). The ester was resolved and hydrolysized to yield the respective enantiopure (+)- and (−) isomers of bicyclic ABA.

In another embodiment, the C4-C5 (using the same carbon numbers as shown in FIG. 2 compound [8]) acetylene bicyclic ABA and analogs may be synthesized from the allylic alcohol of the previous embodiment. As with bicyclic ABA, the synthesis is similar except that the reduction step is omitted. The allylic alcohol was oxidized to an aldehyde, and then further oxidized to an ester. A ketone was introduced at the C-4' carbon (using the same carbon numbers as shown in FIG. 2 compound [8]).

In an additional embodiment, a synthetic route is used to produce a bicyclic ABA ester and analogs that may have a wide range of substituents at the 9'-carbon atom (analogous to 8'-substituted ABA), like analogs resistant to metabolism and the putative metabolite of (+)-bicyclic ABA. With commercially available 2-methyl-1-naphthol as starting material, a methyl substituted ketal, was obtained through oxidation. Alkylation, followed by triple bond reduction, two successive oxidations and deprotection of the ketal leads to an enone. The 9'-methylene group was introduced to the enone to afford the 9'-methylene bicyclic ABA ester.

In another embodiment, a bicyclic ABA analog having the following structure is disclosed:

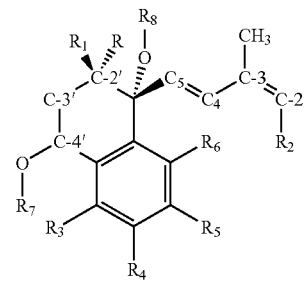

wherein, R or $R_1$ are independently H, X (X=alkyl, alkenyl, alkynyl, aryl, arylalkyl, arylalkenyl, arylalkynyl, cycloalkyl, cycloalkenyl, or cycloalkynyl), XOH, XOX, OH, or $RXR_1$; or wherein, R or $R_1$ do not exist if the other is a double bond to C-2' or if a double bond exists between C-2' and C-3'; or wherein, R or $R_1$ is cyclized with C-3' with the proviso that the resulting cyclized structure is not benzene; wherein, $R_2$ is $CH_2OH$, CHO, COOH or COOX; wherein $R_3$ through $R_6$ are independently H, OH, X, XOH, XOX, OX, $R_3XR_4$, $R_3XR_5$, $R_3XR_6$, $R_4XR_5$, $R_4XR_6$, $R_5XR_6$, halogen, Ohalogen, XOhalogen, or Xhalogen; wherein, $R_7$ is H, X, an additional bond to C-4' to create a carbonyl, or XO cyclized with C-4'; and wherein, $R_8$ is H or methyl.

In a further embodiment, a bicyclic ABA analog having the following structural formula is disclosed, wherein a side chain has a triple bond at C4-C5:

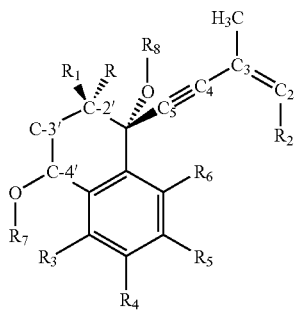

wherein, R or $R_1$ are independently H, X (X=alkyl, alkenyl, alkynyl, aryl, arylalkyl, arylalkenyl, arylalkynyl, cycloalkyl, cycloalkenyl, or cycloalkynyl), XOH, XOX, OH, or $RXR_1$; or wherein, R or $R_1$ do not exist if the other is a double bond to C-2' or if a double bond exists between C-2' and C-3'; or wherein, R or $R_1$ is cyclized with C-3' with the proviso that the resulting cyclized structure is not benzene; wherein, $R_2$ is $CH_2OH$, CHO, COOH or COOX; wherein $R_3$ through $R_6$ are independently H, OH, X, XOH, XOX, OX, $R_3XR_4$, $R_3XR_5$, $R_3XR_6$, $R_5$, $R_4XR_6$, $R_5XR_6$, halogen, Ohalogen, XOhalogen, or Xhalogen; wherein, $R_7$ is H, X, an additional bond to C-4' to create a carbonyl, or XO cyclized with C-4'; and wherein, $R_8$ is H or methyl.

In an additional embodiment, the presence of the aromatic moiety during synthesis of bicyclic ABA analogs, could be used in photoaffinity labeling for the purification of ABA binding proteins is described. Such analogs may incorporate the important functional groups of ABA such as the C-4' carbonyl group and the side chain C-1 carboxyl group in unmodified form (see FIG. 1 compound [1]).

In one embodiment, the bicyclic ABA analog is used for the identification of ABA binding proteins. The bicyclic ABA analog and related compounds may be used for probing the biological activity of ABA and its labile catabolites. In one embodiment, the bicyclic ABA analog or derivatives of the bicyclic ABA analog may be used as affinity probes for isolating ABA receptors and other binding proteins.

In an additional embodiment, the bicyclic ABA analog may be immobilized on a substrate such as, for example a column. Candidate proteins may be placed in contact with the immobilized ABA analog to determine if any of the candidate proteins are ABA binding proteins.

In another embodiment, the bicyclic ABA analogs may be used in photoaffinity labeling. Photoaffinty labeling may be undertaken by employing a chromophore of the tetralone portion of the bicyclic ABA analog. Thus, in an additional embodiment, the linking groups may be attached to the aromatic ring to serve as anchors for other photoaffinity probes.

In yet another embodiment, a process for inhibiting plant cell growth using the bicyclic ABA analogs of the present invention is described. The ability of the bicyclic ABA analogs of the present invention to inhibit plant cell growth may be assayed with a growth inhibition assay. In this embodiment, the bicyclic ABA inhibited the growth of suspension-cultured cells of maize (Black Mexican Sweet) in a dose-dependent manner over a concentration range of 0.1-10.0 μM.

In yet an additional embodiment, the bicyclic ABA analogs of the present invention may be used in a process for inhibiting seed germination. In one embodiment, the bicyclic ABA analog is used in a germination assay of *Arabidopsis thaliana* (Columbia wild type) seeds over a wide range of concentrations (0.33-33 μM).

BEST MODE(S) FOR CARRYING OUT THE INVENTION

Figure 1:
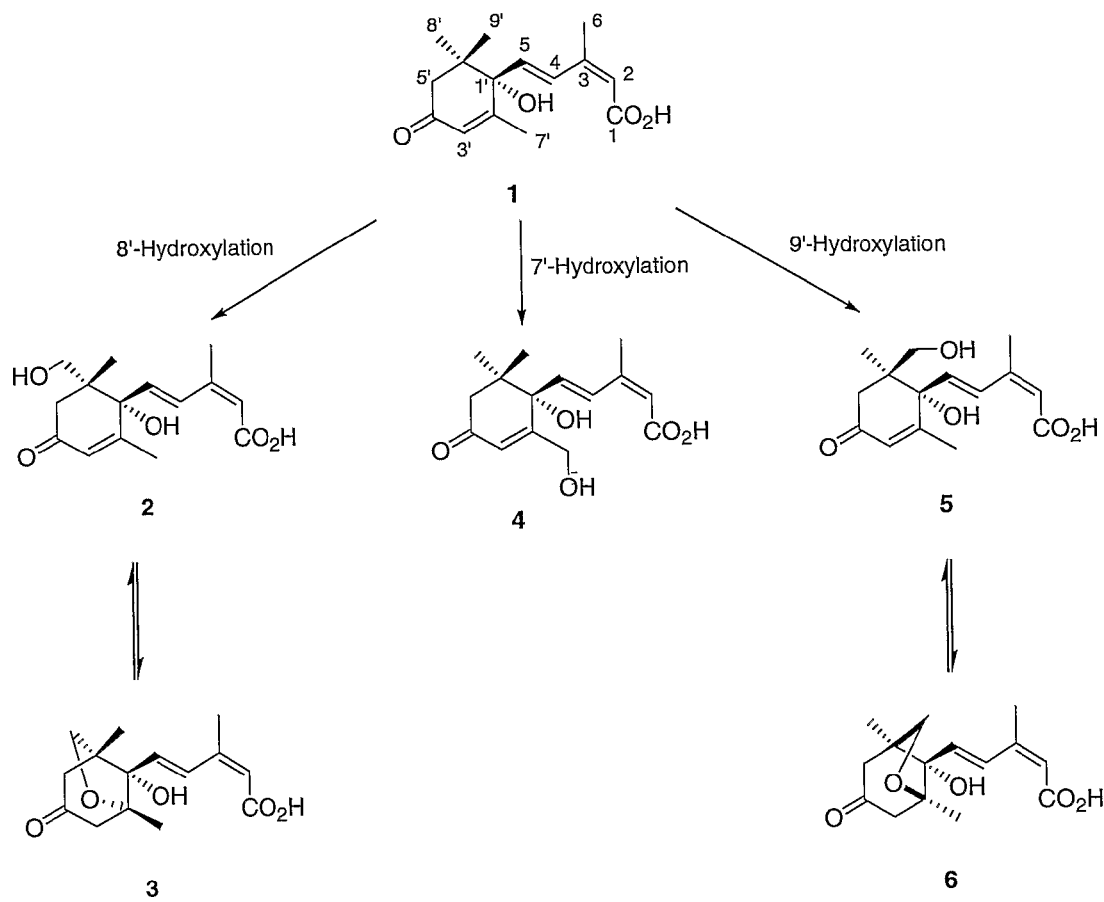
FIG. 1 shows the structure of ABA and illustrates ABA catabolites of ABA catabolism (Scheme 1).
Figure 2:
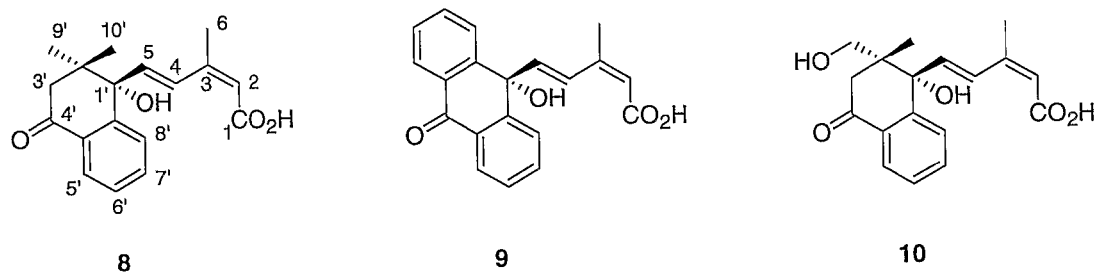
FIG. 2 illustrates the structure of three ABA analogs.

The production of bicyclic ABA and analogs of the present invention may be used in a variety of applications including designing plant growth regulators that will have increased effectiveness, assessing the bioactivity of metabolites, and producing probes for identifying ABA binding proteins. As used herein, bicyclic ABA refers to the (+)-enantiomer of compound [8] in FIG. 2. (+)-bicyclic ABA is used when specifically distinguishing from the (−)-enantiomer of compound [8]. Acetylene bicyclic ABA refers to compound [19] of FIG. 3. Bicyclic ABA ester refers to compound [17] of FIG. 3. Bicyclic ABA analogs encompasses acetylene bicyclic ABA, a bicyclic ABA ester, and any variants of those compounds, or of bicyclic ABA itself. Acetylene bicyclic ABA analogs refers to variations of the acetylene bicyclic ABA. Bicyclic ABA ester analogs refers to variations of the bicyclic ABA ester. Bicyclic ABA analogs is a broader term and not limited to those compounds. When a specific carbon is referenced the numbers will correlate to the carbon numbers as shown in FIG. 2 compound [8], regardless of the moieties attached to the compound. However, when ABA or ABA analogs are referenced the numbers correlate to compound [1] in FIG. 1. It was predicted that bicyclic ABA would be perceived as ABA-like as it had been shown that a related tricyclic analog ABA [9] had weak ABA-like activity in a growth inhibition assay (10). As used herein, brackets [ ] will be used to refer to structures of the FIGS.

In another embodiment, a compound produced using the present invention is illustrated in FIG. 2. It was thought that a P450 monooxygenase in corn cells that hydroxylates ABA may accept bicyclic ABA as a substrate and generate a hydroxymethyl compound [10] (analogous to 8'-hydroxy ABA 2). It was also predicted that the hydroxymethyl derivative would not cyclize to a phaseic acid—like compound, as conjugate addition of the hydroxyl oxygen to the enone would be prevented, preserving the aromaticity of the fused ring, and that compound [10] could be employed in bioassays as a robust analog to probe the role of hydroxylated ABA catabolites.

In a further embodiment, a process for producing bicyclic ABA and analogs is described. The method includes a process illustrated in FIG. 3. Racemic bicyclic methyl abscisate [17] was synthesized from commercially available 1-tetralone [11]. The geminal methyl groups were introduced adjacent to the carbonyl carbon by treatment of 1-tetralone with methyl iodide in the presence of sodium hydride to give the dimethyl tetralone [12] in 83% yield, which is significantly higher than the reported 63% yield when LDA/methyl iodide are used (16 or 17). The side chain was introduced using known methods (5).

Alkylation of the dimethyl tetralone [12] with the dilithium salt of [13] gave the key intermediate [14] in 64% yield. Reduction of the triple bond using sodium bis(2-methoxyethoxy aluminium hydride (RedAL™) yielded the allylic alcohol [15]. Successive oxidations with manganese dioxide to the aldehyde, confirmed by the appearance of an aldehyde doublet in crude $^1$H NMR, and then with a combination of manganese dioxide, sodium cyanide, acetic acid in methanol, gave the ester [16] in 19% yield over three steps. Benzylic oxidation of [16] using a combination of pyridinium dichromate and tert-butyl hydroperoxide yielded racemic methyl ester [17] (17). $^1$H NMR spectrum of the methyl ester [17] shows broadening of peaks, especially the H-4 (δ 7.82 ppm) of the side chain as well as the α-methylene protons at C-3' of the ring (δ 2.5-2.9 ppm), typically a sign of restricted rotation around C-1'. This phenomenon had been observed previously with a C-1' methyl ether ABA analog (18). Through variable temperature $^1$H NMR, the peak broadening for the C-1' methyl ether ABA had been attributed to the barrier to interconversion between conformations with side chain-axial and side chain-equatorial. The ester [17] was resolved by preparative HPLC using a column with a chiral ligand. Base hydrolysis of the enantiomers yielded the respective enantiopure (+)- and (−) isomers of bicyclic ABA acid [8]. The stereochemistry was assigned from x-ray crystallographic analysis of a derivative of the (+)-enantiomer.

Figure 3:
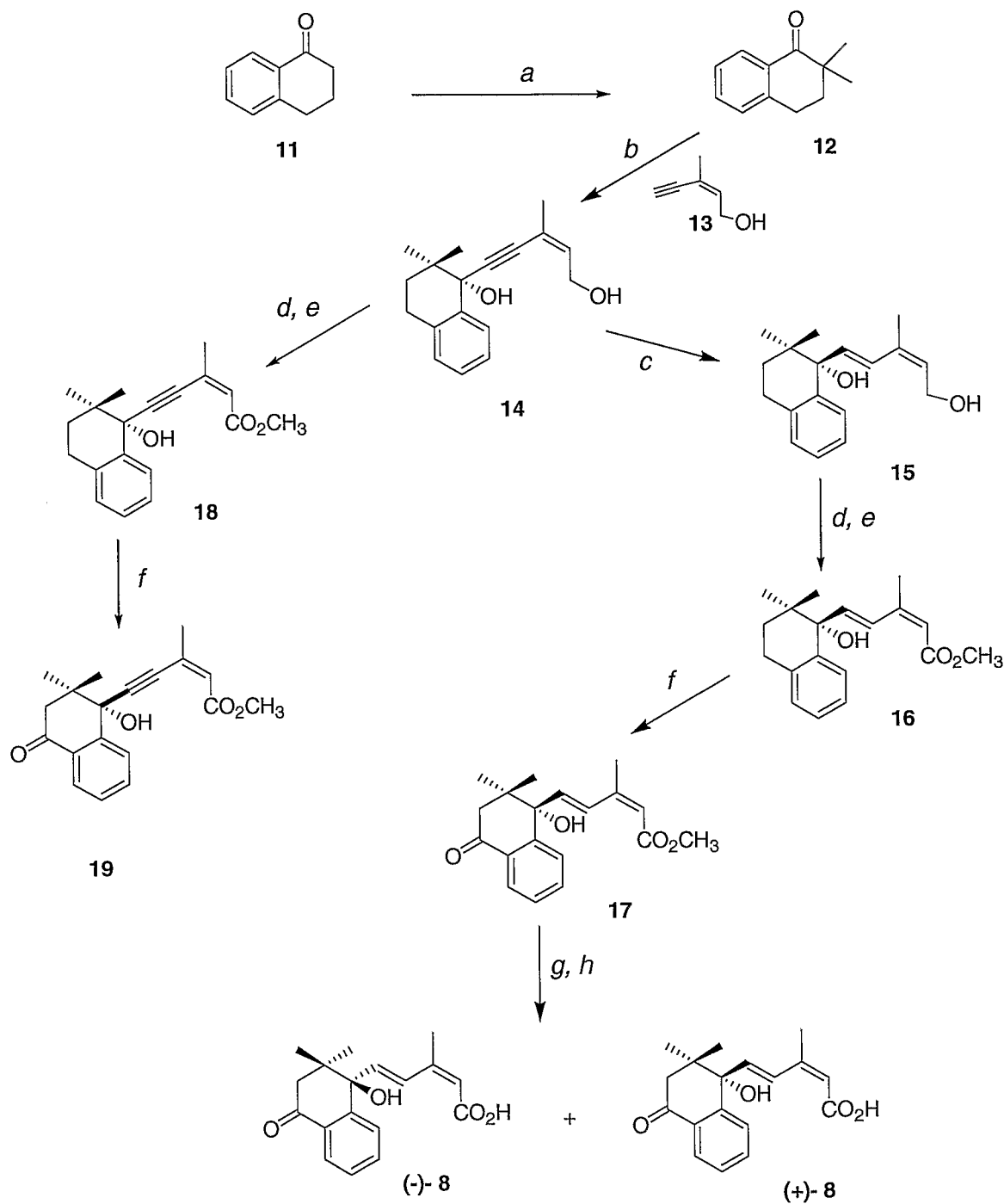
FIG. 3 depicts steps in a process of one embodiment of synthesizing bicyclic ABA and analogs from 1-tetralone. a) $CH_3I$/NaH; b) Dilithium salt of [12]; c) Sodium bis(2-methoxyethoxy) aluminium hydride (RedAL™); d) $MnO_2$; e) $MnO_2$, NaCN, HOAc, $CH_3OH$; f) PDC/tert-BuOOH; g) Chiral HPLC; h) KOH/$CH_3OH$.

In another embodiment shown in FIG. 3, acetylene bicyclic ABA may be synthesized from intermediate [14]. Related C4-C5 acetylenic ABA analogs have been synthesized and showed to exert strong biological activity (18, 19). As with the bicyclic ABA, the synthesis is similar except that the reduction step with sodium bis(2-methoxyethoxy) aluminium hydride (RedAL™) is omitted. An intermediate [14] is oxidized to the ester [18] in 62% over two steps, followed by benzylic oxidation with PDC/tert-butyl hydroperoxide to afford acetylene bicyclic ABA. One of the advantages of acetylene bicyclic ABA and analogs is that the elimination of the reduction step provides a cost efficient synthesis of potentially active analogs.

Figure 4:
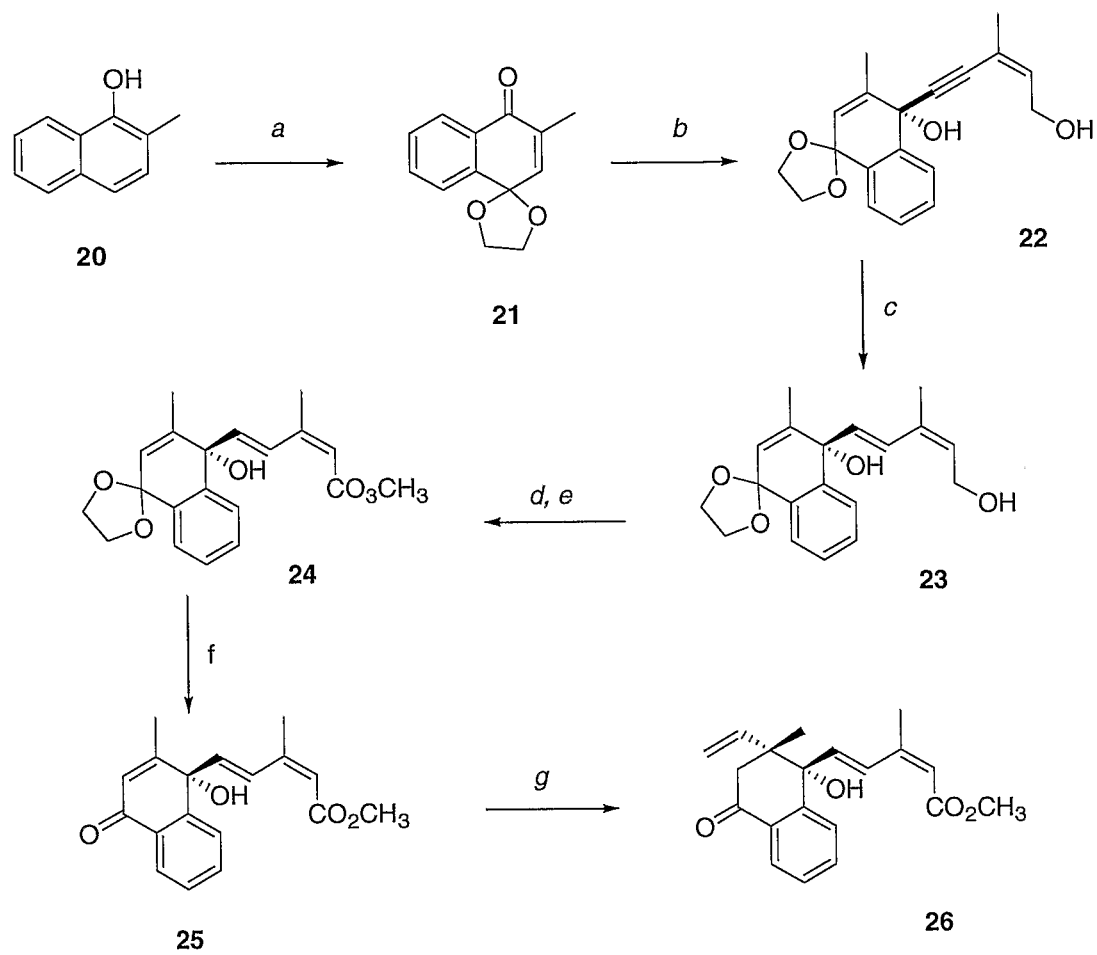
FIG. 4 depicts steps in a process of another embodiment of synthesizing bicyclic ABA analogs from 2-methyl-1-naphthol. a) PhI (OAc)$_2$/Ethylene glycol; b) n-Buli/Side Chain; c) Sodium bis(2-methoxyethoxy) aluminium hydride (RedAL™); d) $MnO_2$; e) $MnO_2$/NaCN/HOAc/MeOH; f) aq 10% HCl; g) VinylMgBr.

In an additional embodiment as shown in FIG. 4, a synthetic route is used to produce bicyclic analogs that may have a wide range of substituents at the 9'-carbon atom (analogous to 8'-substituted ABA), like analogs resistant to metabolism and the putative metabolite of [(+)-8]. More persistent ABA analogs with 8'-methylene and 8'-acetylene substituents have been synthesized and shown to have excellent biological activities (5, 20). For example, with commercially available 2-methyl-1-naphthol (20) as starting material, the methyl substituted ketal [21], was obtained through oxidation using iodobenzene diacetate. Alkylation with the dilithium salt of [13], followed by triple bond reduction to intermediate [23], two successive oxidations and deprotection of ketal [24] leads to the enone [25]. The 9'-methylene group was introduced by the conjugate addition of vinyl magnesium bromide to the enone [25] to afford the 9'-methylene bicyclic ABA [26]. It was shown that such conjugate additions afforded the product with the alkyl group on the same face of the molecule as the hydroxyl group at C-1' (5, 20).

In another embodiment, a bicyclic ABA analog having the following structure is disclosed:

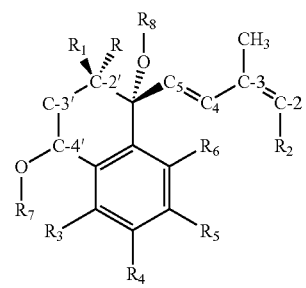

wherein, R or $R_1$ are independently H, X (X=alkyl, alkenyl, alkynyl, aryl, arylalkyl, arylalkenyl, arylalkynyl, cycloalkyl, cycloalkenyl, or cycloalkynyl), XOH, XOX, OH, or $RXR_1$; or wherein, R or $R_1$ do not exist if the other is a double bond to C-2' or if a double bond exists between C-2' and C-3'; or wherein, R or $R_1$ is cyclized with C-3' with the proviso that the resulting cyclized structure is not benzene; wherein, $R_2$ is $CH_2OH$, CHO, COOH or COOX; wherein $R_3$ through $R_6$ are independently H, OH, X, XOH, XOX, OX, $R_3XR_4$, $R_3XR_5$, $R_3XR_6$, $R_4XR_5$, $R_4XR_6$, $R_5XR_6$, halogen, Ohalogen, XOhalogen, or Xhalogen; wherein, $R_7$ is H, X, an additional bond to C-4' to create a carbonyl, or XO cyclized with C-4'; and wherein, $R_8$ is H or methyl.

In a further embodiment, a bicyclic ABA analog having the following structural formula is disclosed, wherein a side chain has a triple bond at C4-C5:

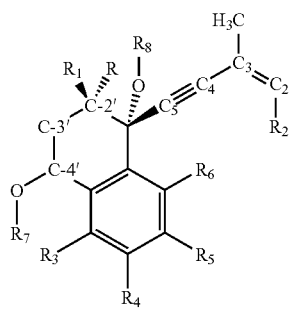

wherein, R or $R_1$ are independently H, X (X=alkyl, alkenyl, alkynyl, aryl, arylalkyl, arylalkenyl, arylalkynyl, cycloalkyl, cycloalkenyl, or cycloalkynyl), XOH, XOX, OH, or $RXR_1$; or wherein, R or $R_1$ do not exist if the other is a double bond to C-2' or if a double bond exists between C-2' and C-3'; or wherein, R or $R_1$ is cyclized with C-3' with the proviso that the resulting cyclized structure is not benzene; wherein, $R_2$ is $CH_2OH$, CHO, COOH or COOX; wherein $R_3$ through $R_6$ are independently H, OH, X, XOH, XOX, OX, $R_3XR_4$, $R_3XR_5$, $R_3XR_6$, $R_4XR_5$, $R_4XR_6$, $R_5XR_6$, halogen, Ohalogen, XOhalogen, or Xhalogen; wherein, $R_7$ is H, X, an additional bond to C-4' to create a carbonyl, or XO cyclized with C-4'; and wherein, $R_8$ is H or methyl.

In an additional embodiment, the presence of the aromatic moiety to synthesize bicyclic ABA analogs, which could be used in photoaffinity labeling for the purification of ABA binding proteins is described. Such analogs may incorporate the important functional groups of ABA such as the C-4' carbonyl group and the side chain C-1 carboxyl group in unmodified form. These analogs are expected to be superior to those used for identifying binding proteins (11, 21-23).

In one embodiment bicyclic ABA and analogs are used for the identification of ABA binding proteins. Bicyclic ABA and analogs may be used for probing the biological activity of ABA and its labile catabolites. This would require the bicyclic ABA and analogs to possess biological activity and be accommodated in an active site of ABA binding proteins. In one embodiment, bicyclic ABA and analogs or derivatives of both ABA analog may be used as affinity probes for isolating ABA receptors and other binding proteins. This may be useful since ABA receptors or binding proteins, are poorly understood (2, 11).

In an additional embodiment, bicyclic ABA and analogs may be immobilized on a substrate such as, for example a column. Candidate proteins may be placed in contact with the immobilized bicyclic ABA and analog to determine if any of the candidate proteins are ABA binding proteins.

In another embodiment, bicyclic ABA and analogs may be used in photoaffinity labeling. Photoaffinity labeling may be undertaken by employing a chromophore of the tetralone portion of the bicyclic ABA and analogs. Related acetophenone and benzophenone compounds have been shown to possess suitable photochemical reactivity. In the presence of 2-propanol, benzophenone and acetophenone were shown to form pinacol products quantitatively under the influence of UV light (12, 13). Thus, in an additional embodiment, the linking groups may be attached to the aromatic ring to serve as anchors for other photoaffinity probes. Attempts have been made to utilize the $\alpha,\beta$-unsaturated carbonyl group of ABA in cross-linking experiments, few ABA binding proteins have yet been identified or reported (14, 15).

Figure 6:
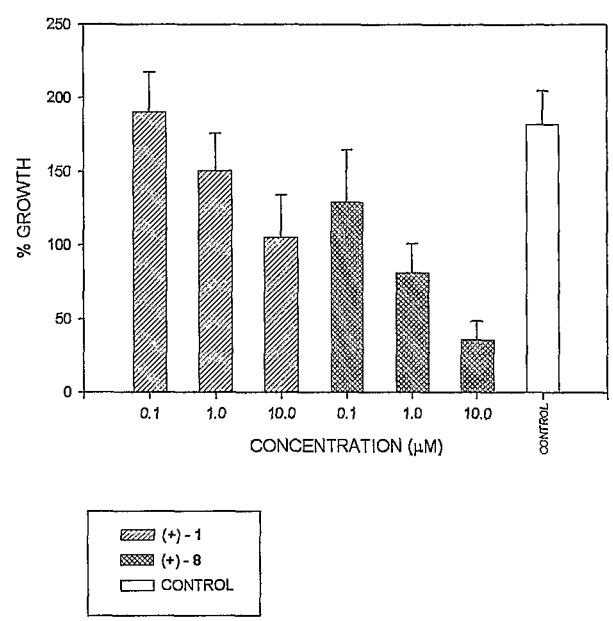
FIG. 6 is a graph of the result of growth inhibition tests using (+)-[1] ABA and (+)-[8] bicyclic ABA analog on BMS maize.

In yet another embodiment, a process for inhibiting plant cell growth using the bicyclic ABA and analogs of the present invention is described. The ability of bicyclic ABA and analogs of the present invention to inhibit plant cell growth may be assayed with a growth inhibition assay. In one assay, suspension-cultured corn cells are used in a well characterized experimental system that has been useful for comparing the biological activity and metabolism of ABA and ABA analogs (6). In this embodiment, bicyclic ABA like (+)-ABA, inhibited the growth of suspension-cultured cells of maize (Black Mexican Sweet) in a dose-dependent manner over a concentration range of 0.1-10.0 µM. As shown in FIG. 6, the bicyclic ABA showed inhibitory activity that is significantly higher (almost 10-fold) than that of (+)-ABA.

Figure 7:
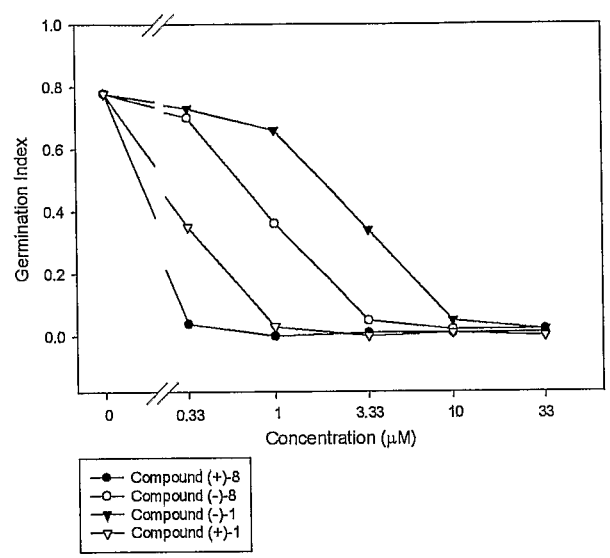
FIG. 7 is a graph of the results of seed germination inhibition tests using (+)-[1] ABA, (−)-[1] ABA, (−)-[8] bicyclic ABA analog, and (+)-[8] bicyclic ABA analog *Arabidopsis* seeds.
Figure 8:
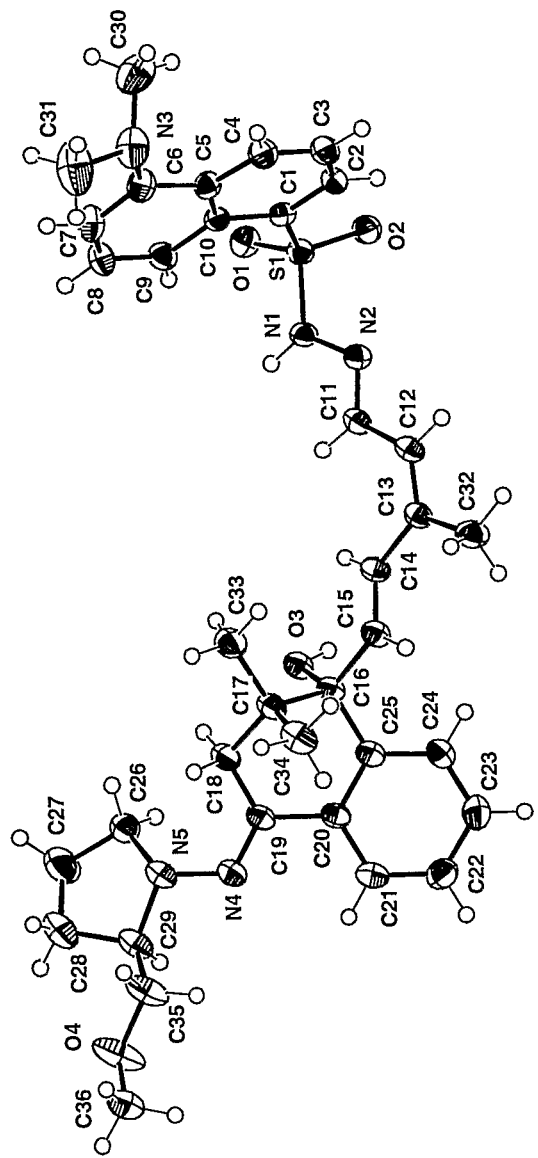
FIG. 8 is an illustration of compound [31] from FIG. 5.

In yet an additional embodiment, bicyclic ABA and analogs of the present invention may be used in a process for inhibiting seed germination. In one embodiment, bicyclic ABA is used in a germination assay of *Arabidopsis thaliana* (Columbia wild type) seeds over a wide range of concentrations (0.33-33 µM). Similar treatments were performed for ABA [1] (both enantiomers) to allow for a direct comparison between ABA and bicyclic ABA (both enantiomers). The results are expressed in terms of germination indices, which summarize the rate and extent of germination over the time of the experiment at a given concentration. As shown in FIG. 7, the (+) enantiomer of bicyclic ABA was highly effective in inhibiting the germination of the seeds over the 7-day test period at all concentrations. The (+) enantiomer of bicyclic ABA is a more effective germination inhibitor than (+) ABA. At the lowest concentration of 0.33 µM, the germination index for (+)-ABA (1) was almost 0.4, compared with less than 0.1 in the case of (+) bicyclic ABA [8]. As expected, the (−) enantiomer of bicyclic ABA was less effective than the corresponding (+) enantiomer, which was only active at concentrations of ≥1 µM. A similar pattern was observed for the (−) enantiomer of ABA [1], which was only effective at concentrations≥3.33 µM. The biological activity of the bicyclic ABA is compared to that of ABA in two assays and found to be more potent.

In each of the various embodiments, the present invention describes processes for synthesizing bicyclic ABA and analogs, as well as using the bicyclic ABA and analogs to inhibit plant growth and seed germination. Additionally, bicyclic ABA and analogs described herein may be utilized in binding ABA proteins. One of ordinary skill in the art will understand that the inventive processes described herein encompass any ABA analog that is not further metabolized within a cell.

In one embodiment, a process described herein produces bicyclic ABA through a 7-step synthetic scheme. This bicyclic ABA is significantly more active than ABA in the two assays in which the compound has been tested as described herein. The additional carbon atoms linking the C-3' and C-7' of ABA (using compound [1] numbering) in the bicyclic analog do not appear to affect adversely the biological activity in either the seed germination or the corn cell growth inhibition assays. Thus, it appears that the binding sites in proteins that perceive or metabolize ABA can accommodate the extra steric bulk of the bicyclic ABA.

Some additional embodiments are the us of bicyclic ABA and analogs for crop improvement such as—

Antitranspirants: reduction of water loss during transplantation or when soil moisture is low or unavailable.

Promotion of root growth and/or increased root-shoot ratio under drought conditions or during seedling establishment.

Increasing survival and reducing damage under sub-optimal growth conditions, especially due to temperature and other abiotic stresses.

Regulation of germination/dormancy, for example by: Preventing preharvest sprouting by maintaining dormancy Enabling fall seeding of spring crops by inhibiting premature germination Potential herbicidal activity either by preventing weed growth until crops are established or by hormonal toxicity.

Production of seed products, by increasing production of seed proteins and lipids during embryo development, including increased expression of ABA-dependent transgenes.

Production of artificial seed for micropropagation. Facilitating desiccation of somatic embryos and normal development in culture.

Affinity labeling reagents for identifying proteins involved in ABA action and metabolism.

Example 1

Acts of one embodiment of a process for producing bicyclic ABA and analogs as shown in FIG. 3.

Production of
2,2-Dimethyl-3,4-dihydro-2H-naphthalen-1-one [12]

To a suspension of NaH (8.2 gm, 343 mmol) in THF (250 mL) in a one-liter round bottomed flask, 1-tetralone [11] (10.0 gm, 69 mmol) dissolved in dry THF (25 mL) was added.

After stirring the mixture for 10 minutes at RT, methyl iodide (11.1 ml, 178 mmol) was added via a syringe. The mixture was heated on an oil bath to 40° C. for 30 minutes, and stirring continued at RT until the starting material disappeared. The reaction was monitored by TLC using ethyl acetate:hexane (1:6) solvent mixture. The reaction was quenched by addition of water (slowly and dropwise) to destroy excess sodium hydride. The mixture was extracted with ethyl acetate, washed with water and dried over sodium sulphate. Evaporation of the solvent yielded a brown oil. Column chromatography using silica gel with EtOAc:Hexane (1:6) afforded clean 2,2-dimethyl-1-tetralone [12](10.8 g, 83%).

FTIR ($\lambda_{max}$): 2956, 1682, 1601 cm$^{-1}$.

$^1$H NMR (500 MHz, CDCl$_3$); 1.20 (s, 6H, 2×CH$_3$), 1.97 (t, 2H, J=6.5 Hz, 2 H-3), 2.97 (t, 2H, J=6.5 Hz, 2 H-4), 7.21 (d, 1H, J=7.5 Hz, ArH-5), 7.28 (t, 1H, J=7.5 Hz, ArH-6), 7.45 (t, 1H, J=7.5 Hz, ArH-7) and 8.03 (d, 1H, J=7.5 Hz, ArH-8).

HRMS: Calculated for C$_{12}$H$_{14}$O, 174.1045, Found: 174.1031.

The production of (2Z)(1R)-1-(5-Hydroxy-3-methyl-pent-3-en-1-ynyl)-2,2-dimethyl-1,2,3,4-tetrahydro-naphthalen-1-ol [14]

(Z)-3-Methylpent-2-en-4-yn-1-ol [13] (5.0 g, 52 mmol) in dry THF (300 mL) was cooled to −78° C. under an atmosphere of argon. n-Butyl lithium (70.0 mL, 1.6 M in hexanes, 112 mmol) was added slowly, via syringe. The mixture was allowed to stir at −78° C. for 45 minutes, after which, 2,2-dimethyl-1-tetralone [12] (7.5 g, 43 mmol), dissolved in 50 mL dry THF was added. The mixture was stirred for a further 15 minutes at −78° C. and the ice bath was removed. The reaction mixture was stirred at RT for a further 3 hr, by which point, starting material had disappeared. The reaction was quenched by addition of a saturated solution of ammonium chloride. The mixture was stirred for 10 minutes and extracted with ethyl acetate (3×150 mL), washed with water (2×200 mL) and dried over anhydrous Na$_2$SO$_4$. Evaporation of the solvent yielded the desired alcohol as a brown oil. Column chromatography of the brown oil using silica gel with ethyl acetate:hexane (1:2) gave allylic alcohol [14] (6.1 g, 78.2%).

FTIR ($\lambda_{max}$ cm$^{-1}$): 3383, 3067, 2941, 2278.

$^1$H NMR (500 MHz, CDCl$_3$); 1.07 (s, 3 H-9'/10'), 1.15 (s, 3H-9'/10'), 1.64-1.68 (m, 1 H-3'), 1.88 (s, 3 H-6), 1.97-2.12 (m, 1 H-3'), 2.80-2.88 (m, 2 H-4'), 4.27 (d, J=6.7 Hz, 2 H-1), 5.84 (t, J=6.7 Hz, 1 H-2), 7.08 (m, ArH-5'), 7.20 (m, 2 ArH-6' and 7') and 7.77 (m, ArH-8').

HRMS: Calculated for C$_{18}$H$_{21}$O$_2$: 269.1542 (M−1); Found 269.1536.

The production of Methyl-(2Z,4E)-5-((1S)-1-Hydroxy-2,2-dimethyl-1,2,3,4-tetrahydro-naphthalen-1-yl)-3-methyl-penta-2,4-dienoate [16]

The allylic alcohol 14 (6.0 g, 22.1 mmol) in dry THF was cooled to −78° C. and sodium bis(2-methoxyethoxy) aluminium hydride (RedAL™)(13.7 ml, 44.2 mmol) added dropwise via syringe. The reaction mixture was stirred at −78° C. for 1 hr and the allowed to warm up to 0° C. and stirred for a further 2 hr. The reaction was quenched by slow addition of water (100 mL) and extracted with diethyl ether (2×200 mL). The organic phase was washed with water (2×200 mL) and dried over anhydrous Na$_2$SO$_4$. Evaporation of solvent left a crude brown oil of the allylic alcohol [15] (6.05 g), which was carried through to the next stage without any further purification.

The crude allylic alcohol [15] (6.05 g, 22.2 mmol) was dissolved in dry acetone (250 mL) and manganese dioxide (38.7 g, 445 mmol) was added. The mixture was stirred at RT for 3 hr, after which all the starting material had disappeared. The black suspension was filtered through a bed on Celite®. Evaporation of solvent left a clear brown oil of the aldehyde (4.29 g), which was carried through to the next stage without any further purification. $^1$H NMR of the crude mixture showed the presence of an aldehyde proton.

To the aldehyde (4.29 g, 15.9 mmol), dissolved in methanol (150 mL), were added, manganese dioxide (27.7 g, 318.0 mmol), sodium cyanide (2.80 g, 57.2 mmol) and glacial acetic acid (1.05 g, 17.5 mmol). The mixture was stirred at RT for 4 hrs, after which all the starting material had disappeared. The suspension was filtered over a bed of Celite® and washed with methanol (3×100 mL). The combined filtrate was concentrated under vacuo to yield a light brown solid. Water (150 mL) was added to the crude solid and then extracted with ethyl acetate (3×200 mL). The organic phase was washed with water (3×100 mL) and dried over anhydrous Na$_2$SO$_4$. Evaporation of solvent yielded a brown oil. Column chromatography using silica gel and 25% ethyl acetate in hexane gave the desired bicyclic ABA ester [16] (3.3 g, 49.3%) over the three steps.

FTIR ($\lambda_{max}$ cm$^{-1}$): 3402, 3070, 2951, 1710, 1599.

$^1$H NMR (500 MHz, CDCl$_3$); 0.96 (s, 3 H-9'/10'), 1.00 (s, 3 H-9'/10'), 1.66-1.70 (m, 1 H-3'), 1.82-1.90 (m, 1 H-3'), 1.98 (s, 3 H-6), 2.86 (t, J=6.8 Hz, 2 H-4'), 3.67 (s, 3 H, CO$_2$CH$_3$), 5.68 (s, 1 H-2), 6.30 (d, J=16.0 Hz, 1 H-5), 7.09-7.20 (m, 3 ArH-5', 6' and 7'), 7.36 (dd, J=6.5 and 1.1 Hz, ArH-8') and 7.79 (d, J=16.0 Hz, 1 H-4).

HRMS: Calculated for C$_{19}$H$_{24}$O$_3$, 300.1725. Found: 300.1721.

The production of Methyl-(2Z,4E)-5-((1S)-1-Hydroxy-2,2-dimethyl-4-oxo-1,2,3,4-tetrahydro-naphthalen-1-yl)-3-methyl-penta-2,4-dienoate [17]

To the ester [16] (3.0 g, 10 mmol) dissolved in benzene (100 mL), were added, pyridinium dichromate (5.64 g, 30 mmol) and tert-butyl hydroperoxide (1.35 g, 15 mmol). The mixture was stirred at RT for 4 hr. Diethyl ether (50 mL) was added to the reaction mixture and stirring continued for a further 30 min. The mixture was filtered through a bed of Celite® and washed with diethyl ether (3×25 mL). The combined organic filtrate was concentrated in vacuo, leaving a brown oil. Column chromatography of the brown oil using silica gel with 25% ethyl acetate in hexane afforded the unreacted starting material (1.20 g) with R$_f$ 0.5 and the desired ester [17] (1.48 g, 78%), based on amount of starting material consumed. IR ($\lambda_{max}$ cm$^{-1}$): 3457, 3067, 2962, 1722, 1682, and 1599. $^1$H NMR (500 MHz, CDCl$_3$); 1.06 (s, 3 H-9'/10'), 1.07 (s, 3 H-9'/10'), 1.98 (s, 3 H-6), 2.56 (d, J=17.1 Hz, 1 H-3'), 2.80 (d, 17.1 Hz, 1 H-3'), 3.66 (s, 3 H, CO$_2$CH$_3$), 5.72 (s, 1 H-2), 6.35 (d, J=16.0 Hz, 1 H-5), 7.42 (t, J=7.1 Hz, ArH-7'), 7.54-7.59 (m, 2 ArH-6' and 8'), 7.82 (d, J=15.9 Hz, 1 H-4) and 8.03 (dd, J=7.9 and 0.7 Hz, ArH-5').

HRMS: Calculated for C$_{19}$H$_{22}$O$_4$: 314.1518. Found: 314.1521.

The enantiomers of ester [17] were resolved by chiral HPLC (Chiralcel™ AS column (10×250 mm; Daicel Chemical Industries, Ltd., iso-PrOH-Hexane, 3:97) and had the following optical rotations: [α]$_D$=+247.2 (c 1.23, CHCl$_3$) (retention time 12.5 min) and −242.6 (c 1.03, CHCl$_3$) (retention time 15.8 min) for (+)-17 and (−)-17, respectively.

The production of (2Z,4E)-5-((1S)-1-Hydroxy-2,2-dimethyl-4-oxo-1,2,3,4-tetrahydro-naphthalen-1-yl)-3-methyl-penta-2,4-dienoic acid (+)-[8]

A mixture of ester (+)-[17] (0.05 g, 0.159 mmol) in MeOH (4 mL) and 1.0 M KOH (4 mL) was stirred at 45° C. for 2 hr, by which point, all the starting material had disappeared. The solvent was evaporated at reduced pressure, the aqueous layer acidified to pH 3 with 10% HCl and extracted with ethyl acetate (3×50 mL). The combined organic extracts were dried over anhydrous $Na_2SO_4$, and concentrated to provide acid (+)-8 (0.037 g, 76%). IR ($\lambda_{max}$, $cm^{-1}$): 3606-2488, 3453, 1685, 1598.

$^1$H NMR (500 MHz, $CDCl_3$); 1.06 (s, 3 H-9'/10'), 1.08 (s, 3 H-9'/10'), 2.02 (s, 3H-6), 2.56 (d, J=17.2 Hz, 1 H-3'), 2.80 (d, J=17.0 Hz, 1 H-3'), 5.72 (s, 1 H-2), 6.42 (d, J=16.0 Hz, 1 H-5), 7.38-7.41 (m, ArH-6'/7'), 7.52-7.59 (m, 2 ArH-7' and 8'), 7.74 (d, J=16.0 Hz, 1 H-4) and 8.02 (dd, J=7.8 and 1.2 Hz, ArH-5'). $^{13}$C NMR $CDCl_3$; 21.4, 23.4, 24.3, 41.1, 49.7, 60.4, 78.4, 117.7, 126.7, 127.2, 128.2, 128.4, 130.9, 134.5, 139.2, 145.6, 151.8, 171.0 and 197.4

HRMS: Calculated for $C_{18}H_{20}O_4$, 300.1362: Found: 300.1351.

The production of 5-(1-Hydroxy-2,2-dimethyl-1,2,3,4,-tetrahydro-naphthalen-1-yl)-3-methyl-pent-2-en-4-ynoic acid methyl ester [18]

To a solution of alcohol [14] (9.0 g, 33.3 mmol) in acetone (150 mL) was added manganese dioxide (58 g, 667 mmol) in portions. The mixture was stirred for 21 hr at RT, filtered through a bed of Celite® and washed with acetone (2×100 mL). The combined filtrates and washings were evaporated to give a crude product as a brown oil (7.33 g) the crude product was used in the next step without further purification. A small sample was purified by flash chromatography (15% ethyl acetate in hexane) to provide pure aldehyde.

FTIR ($\lambda_{max}$ $cm^{-1}$): 3434, 3056, 2966, 2211, 1667, 1594, 1454, 1385, 763, 722.

$^1$H NMR (500 MHz, $CDCl_3$): 1.10 (s, 3 H-9'/10'), 1.16 (s, 3 H-9'/10'), 1.65 (m, 1H-3'), 2.00 (m, 1 H-3'), 2.14 (s, 3 H-6), 2.85 (m, 2 H-4'), 6.16 (d, J=7.25 Hz, 1 H-2), 7.11 (m, ArH-5'/6'/7'), 7.23 (m, 2 ArH-5'/6'/7'), 7.73 (m, ArH-8'), 9.91 (d, J=7.25 Hz, 1 H, CHO), $^{13}$C NMR ($CDCl_3$): 192.5, 142.2, 138.0, 135.2, 134.9, 129.1, 128.1, 128.0, 126.5, 103.0, 82.8, 75.1, 37.6, 31.2, 25.6, 24.8, 23.8, and 23.3.

To a solution of the aldehyde (7.33 g, 27.4 mmol) in methanol (180 mL) were added NaCN (3.35 g, 68.4 mmol), glacial acetic acid (1.8 g, 30.1 mmol), and manganese dioxide (35.7 g, 410.3 mmol). The reaction mixture was stirred at RT for 21 hr, filtered through a bed of Celite® and washed with methanol (2×100 mL). The combined filtrate and washings were evaporated to give a light brown residue. $H_2O$ (200 mL) was added to the residue and extracted with ethyl acetate (3×100 mL), dried over anhydrous $MgSO_4$ and concentrated in vacuo to afford crude product (8.25 g) which was purified by flash chromatography (15% ethyl acetate in hexane) to give pure ester [18] (6.14 g, 62% over two steps).

FTIR ($\lambda_{max}$ $cm^{-1}$): 3450, 3060, 2954, 2209, 1706, 1618, 1448, 1375, 776, 763.

$^1$H NMR (500 MHz, $CDCl_3$): 1.11 (s, 3 H-9'/10'), 1.18 (s, 3 H-9'/10'), 1.71 (m, 1H-3'), 2.02 (m, 1 H-3'), 2.04 (s, 3 H-6), 2.65 (s, br, 1 H, OH), 2.84 (m, 2 H-4'), 3.69 (s, 3H, $CO_2CH_3$), 5.98 (s, 1 H-2), 7.09 (m, 1 ArH-5'/6'/7'), 7.21 (m, 2 ArH-5'/6'/7'), 7.87 (m, ArH-8').

$^{13}$C NMR ($CDCl_3$): 165.2, 138.5, 134.8, 134.5, 128.7, 125.5, 127.6, 126.1, 123.9, 103.2, 85.0, 74.9, 51.1, 37.4, 31.1, 25.6, 25.0, 23.7, and 23.3.

The production of 5-(1-Hydroxy-2,2-dimethyl-4-oxo-1,2,3,4-tetrahydro-naphthalen-1-yl)-3-methyl-pent-2-en-4-ynoic acid methyl ester [19]

To a solution of ester [18] (1.43 g, 4.8 mmol) in benzene (60 mL) were added PDC (7.22 g, 19.2 mmol), tert-butyl hydroperoxide (70% in water, 2.5 g, 19.2 mmol), and Celite® (5.0 g). The reaction mixture was stirred at RT for 4 hr and filtered, washed with benzene (30 mL). The combined filtrate and washings were concentrated to a volume of about 60 mL. To this solution were added PDC (7.22 g, 19.2 mmol), tert-butyl hydroperoxide (70% in water, 2.5 g, 19.2 mmol) and Celite® (5.0 g). The reaction mixture was stirred for an additional 3 hr and ether (50 mL) added. After 30 min, the reaction suspension was filtered and washed with ether (2×100 mL). The combined filtrate and washings were evaporated to give a brown residue, which was purified by flash chromatography (20% ethyl acetate in hexane) to provide ester [18] (0.47 g, 33%) and the product [19] (0.74 g, 49%).

FTIR ($\lambda_{max}$ $cm^{-1}$): 3436, 3068, 2967, 2213, 1685, 1618, 1598, 1450, 1223, 854, 770.

$^1$H NMR (CDCl3): δ 1.20 (s, 6 H-9' and 10'), 2.03 (s, 3 H-6), 2.73 (m, br, 1 H-3'), 2.88 (m, br, 1 H-3'), 3.69 (s, 3 H, $CO_2CH_3$), 6.03 (s, 1 H-2), 7.43 (m, ArH-6'/7'), 7.62 (m, ArH-6'/7'), 8.00 (m, 2 ArH-5' and 8').

$^{13}$C NMR ($CDCl_3$): 197.2, 165.2, 143.7, 134.3, 134.1, 130.1, 128.5, 127.6, 126.7, 124.9, 100.5, 86.5, 74.7, 51.4, 48.5, 41.5, 24.9, 24.9, 23.0.

Example 2

Another embodiment of a process for producing a bicyclic ABA analog as shown in FIG. 4.

The production of 2-Methyl-4,4-ethylenedioxynaphthalen-1-one [21]

2-Methyl-1-naphthol [20] (5.0 g, 31.6 mmol) dissolved in ethylene glycol (100 mL) was added to a round bottomed flask (500 mL), containing iodobenzene diacetate (21.4 g, 66.4 mmol) dissolved in ethylene glycol (100 mL) and stirred with a mechanical stirrer at RT for 4 hr. Reaction was quenched by addition of $H_2O$ (50 mL) followed by extraction with diethyl ether (3×150 mL). The organic phase was washed with saturated NaCl solution (2×200 mL), dried over anhydrous $Na_2SO_4$ and dried in vacuo. Flash chromatography using silica gel with 50% ether in hexane yielded [21] (4.4 g, 64.3%.

FTIR ($\lambda_{max}$ $cm^{-1}$): 3290, 3074, 2984, 2910, 1658.

$^1$H NMR (500 MHz, $C_6D_6$): 1.84 (s, 3H, H-2), 3.55-3.67 (m, 4H, $OCH_2CH_2O$), 6.29 (s, 1H, H-3), 7.01 (t, 1H, J=7.8 Hz, ArH-6), 7.15 (t, 1H, J=7.8 Hz, ArH-7), 7.48 (d, 1H, J=7.8 Hz, ArH-5) and 8.22 (dd, 1H, J=7.8, 0.8 Hz, ArH-8).

HRMS: Calculated for $C_{13}H_{12}O_3$, 216.0786: Found: 216.0790.

(Z)-3-Methylpent-2-en-4-yn-1-ol (1.3 g, 14.0 mmol) in dry THF (150 mL) was cooled to −78° C. under an atmosphere of argon. 2.5 M n-Butyl lithium (11.2 mL, 28.0 mmol) was added slowly, via syringe. The mixture was allowed to stir at −78° C. for 30 minutes, after which, compound [21] (2.0 g, 9.3 mmol), dissolved in dry THF (50 mL) was added. The mixture was stirred for a further 15 minutes at −78° C. and the ice bath was removed. The reaction mixture was stirred at RT for a further 3 hr, at which point, starting material had disappeared. Reaction was quenched by addition of a saturated solution of $NH_4Cl$. The mixture was stirred for 10 minutes and extracted with ethyl acetate (3×150 mL), washed with $H_2O$ (2×200 mL) and dried over anhydrous $Na_2SO_4$. Evaporation in vacuo afforded a crude brown oil of the allylic alcohol [22], which was used in next stage without further purification.

The production of 1-(5-hydroxy-3-methyl-penta-1,3-dienyl)-2-methyl-4,4-ethylenedioxynaphthalen-1-ol [23]

To the crude oil [22] dissolved in dry THF (50 mL) at −78° C., in a round bottomed flask, was added sodium bis(2-methoxyethoxy) aluminium hydride (RedAl™)(4.0 mL, 14.0 mmol) and mixture stirred for 2 hr. The reaction was stirred for a further 2 hr at 0° C. The reaction was quenched by addition of $H_2O$ (20 mL) followed by extraction with diethyl ether (3×100 mL). The organic phase was washed with saturated NaCl solution (2×100 mL), dried over anhydrous $Na_2SO_4$ and dried in vacuo. Flash chromatography using silica gel with ether yielded allylic alcohol [23] (1.7 g, 58.6%) over two steps. Mp=116-118° C.

FTIR ($\lambda_{max}$ cm$^{-1}$): 3417, 2974, 2882, 1677.

$^1$H NMR (500 MHz, CDCl$_3$): 1.50 (s, 3H, H-2'/3), 1.63 (s, 3H, H-2'/3), 3.59-3.71 (m, 4H, OCH$_2$CH$_2$O), 4.14 (d, 2H, J=Hz, H-1), 5.31 (t, 1H, J=Hz, H-2), 6.05 (d, 1H, J=Hz, H-5), 7.01 (d, 1H, J=Hz, H-4), 6.98 (t, 1H, J=7.8 Hz, ArH-6'/7'), 7.15 (t, 1H, J=7.8 Hz, ArH-6'/7'), 7.53 (d, 1H, J=7.8 Hz, ArH-8') and 7.23 (dd, 1H, J=7.8, 0.7 Hz, ArH-5').

HRMS: Calculated for $C_{19}H_{22}O_4$, 314.1518: Found: 314.1519.

The production of 5-(1-Hydroxy-2-methyl-4-oxo-1,4-dihydro-naphthalen-1-yl)-3-methyl-penta-2,4-dienoic acid methyl ester [25]

The allylic alcohol [23] (1.7 g, 5.4 mmol) was dissolved in dry acetone (100 mL) and manganese dioxide (9.4 g, 108 mmol) was added. The mixture was stirred at RT for 3 hr, after which all the starting material had disappeared. The suspension was then filtered through a bed on Celite®. Evaporation of solvent left a clear brown oil of the aldehyde (1.57 g), which was carried through to the next stage without any further purification. $^1$H NMR of the crude mixture showed the presence of an aldehyde proton.

To the aldehyde (1.6 g, 5.0 mmol), dissolved in methanol (50 mL), were added, manganese dioxide (6.5 g, 75.0 mmol), NaCN (0.6 g, 12.0 mmol) and glacial acetic acid (287 µL, 5.0 mmol). The mixture was stirred at RT for 4 hrs, after which all the starting material had disappeared. The suspension was filtered over a bed of Celite® and washed with methanol (3×50 mL). The combined filtrate was then concentrated in vacuo to yield a light brown solid. Water (100 mL) was added to the crude solid and extracted with ethyl acetate (3×100 mL). The organic phase was washed with water (2×100 mL) and dried over anhydrous $Na_2SO_4$. Evaporation of solvent yielded 1.4 g of brown oil of the ketal ester [24].

To the above oil (ester/ketal) in THF (50 mL) in an ice bath, was added 10% HCl (2 mL) and mixture stirred for 1 hr, after which all starting material had disappeared. $H_2O$ (20 mL) was added to mixture and extracted with diethyl ether (3×100 mL). The organic phase was washed with saturated NaCl (100 mL) and dried over anhydrous $Na_2SO_4$ and dried in vacuo. Flash chromatography using silica gel with 3:1 (diethyl ether-hexane) mixture afforded enone [25] (1.2 g, 74.5%) over three steps. Mp=147-148° C. (EtOAc).

FTIR ($\lambda_{max}$ cm$^{-1}$): 3402, 3070, 2951, 1710, 1657, 1599.

$^1$H NMR (500 MHz, CDCl$_3$): 1.87 (s, 3H, H-2'/3), 2.08 (s, 3H, H2'/3), 3.67 (s, 3H, CO$_2$CH$_3$), 5.69 (s, 1H, H-2/3'), 5.75 (d, 1H, J=15.9 Hz, H-5), 6.21 (s, 1H, H2/3'), 7.39 (t, 1H, J=7.8 Hz, ArH-6'/7'), 7.54 (t, 3H, J=7.8 Hz, ArH-6'/7'), 7.64 (d, 1H, J=7.8 Hz, ArH-8'), 8.01 (d, 1H, J=7.8 Hz, ArH-5') and 8.09 (d, 1H, J=15.9 Hz, H-4).

$^{13}$C NMR (CDCl$_3$): 18.6, 20.9, 51.2, 73.4, 118.2, 126.1, 126.4, 126.8, 127.5, 128.2, 129.4, 133.1, 138.4, 145.8, 149.6, 160.6, 166.4 and 183.9.

HRMS: Calculated for $C_{18}H_8O_4$, 298.1205: Found: 298.1190.

The production of 5-(1-Hydroxy-2-methyl-4-oxo-2-vinyl-1,2,3,4-tetrahydro-naphthalen-1-yl)-3-methyl-penta-2,4-dienoic acid methyl ester [26]

To a round-bottomed flask containing enone [25] (1.1 g, 3.6 mmol) in dry THF (50 mL) at −78° C., was added vinyl magnesium bromide (18.0 mL, 18.0 mmol). After stirring for 1.5 hr, all the starting material had disappeared. The reaction mixture was warmed up to RT and quenched by the addition of saturated NH$_4$Cl (25 mL), followed by extraction with diethyl ether (3×100 mL). The organic phase was washed with saturated NaCl (2×100 mL), dried over anhydrous Na$_2$SO$_4$ and dried in vacuo, leaving a yellow oil (0.890 g). Flash chromatography using silica gel with 50% diethyl ether in hexane yielded the bicyclic 8'-methylene ABA ester 26 (0.69 g, 57.5%). IR ($\lambda_{max}$ cm$^{-1}$): 3473, 2949, 1686, 1635, 1601.

$^1$H NMR (500 MHz, CDCl$_3$): 1.21 (s, 3H, H-10'), 1.97 (s, 3H, H-6), 2.70 (d, 1H, J=17.2 Hz, H-3'), 2.88 (d, 1H, J=17.2 Hz, H-3'), 3.64 (s, 3H, CO$_2$CH$_3$), 5.20 (d, 1H, J=17.5 Hz, H-11' trans to H-9'), 5.22 (d, 1H, J=10.9 Hz, H-11 cis to H-9'), 5.70 (s, 1H, H-2), 5.91 (dd, 1H, J=17.5, 10.9 Hz, H-9'), 6.29 (d, 1H, J=16.0 Hz, H-5), 7.40 (m, 1H, ArH-6'/7'), 7.57 (m, 2H, ArH-6'/7'/8'), 7.70 (d, 1H, J=16.0 Hz, H-4) and 8.03 (d, 1H, J=7.8 Hz, ArH-5').

HRMS: Calculated for $C_{20}H_{22}O_4$, 326.1518: Found: 326.1516.

Regarding Examples 1 AND 2

Melting points are uncorrected. FTIR spectra were recorded using KBr cells on a Perking Elmer Paragon 1000. $^1$H NMR and $^{13}$C were recorded on a Bruker AM 500 MHz Spectrometer. Chemical shifts (δ) and coupling constants (J) are reported as if they are first order. High-resolution mass spectra (HRMS) were recorded in either electron impact (EI) mode, chemical ionization (CI) mode or in negative ion electrospray mode using capillary voltage of 2.75 KV, counter electrode 35 V, collision energy (ELAB) of 14 V and cell pressure of 1.0×10−3 mBar with argon. Mass spectra data are reported in mass to charge units (m/z). IR spectra were obtained with a Perkin-Elmer 237B instrument. Optical rotations were obtained from a Perkin-Elmer 141 Polarimeter and were carried out in chloroform.

Flash chromatography was performed using Merck Silica gel 60 (230-400 mesh). Merck silica gel 60 F$_{254}$ plates (0.2 mm) with aluminum sheet backing were used in analytical TLC. UV active material was detected under UV lamp. The plates were dipped into a solution of phosphomolybdic acid and heated on a hot plate to visualize the spots. Melting points were measured on an Electrothermal 9300 melting point apparatus and are not corrected. The solvent tetrahydrofuran (THF) was dried by distillation from sodium and benzophenone.

Growth Inhibitor

The growth inhibition assay using suspension-cultured corn cells is a well characterized experimental system that has been very useful for comparing the biological activity and metabolism of ABA and ABA analogs (6). As disclosed herein, (+)-bicyclic ABA, like (+)-ABA, produced with the process of the present invention inhibited the growth of suspension-cultured cells of maize (Black Mexican Sweet) in a dose-dependent manner over a concentration range of 0.1-10.0 µM. As shown in FIG. 6, the analog (+)-[8] showed inhibitory activity that is significantly higher (almost 10-fold) than that of (+)-ABA.

Maize cell cultures were treated as described by Balsevich et. al. (6). The cultures were incubated on a rotary shaker for 4 days, and the cells were separated from the medium by vacuum filtration and weighed immediately. The effect of ABA and bicyclic ABA on cell growth was determined at various concentrations (0-10 µM) by calculating the percentage increase in fresh weight [(final weight×100/initial weight)−100)]. Measurements were performed in triplicate and average values were normalized to a control (untreated) value of 100%.

Germination Inhibition

Bicyclic ABA produced using the process of the present invention was also studied in a germination assay of *Arabidopsis thaliana* (Columbia wild type) seeds over a wide range of concentrations (0.33-33 µM) (FIG. 7). Similar treatments were performed for ABA [1] (both enantiomers) to allow for a direct comparison between ABA and bicyclic ABA (both enantiomers). The results are expressed in terms of germination indices, which summarize the rate and extent of germination over the time of the experiment at a given concentration. As shown in FIG. 7, the (+) enantiomer of bicyclic ABA [8] was highly effective in inhibiting the germination of the seeds over the 7-day test period at all concentrations. The (+) enantiomer of [8] is a more effective germination inhibitor than (+) ABA. At the lowest concentration of 0.33 µM, the germination index for (+)-ABA [1] was almost 0.4, compared with less than 0.1 in the case of (+) bicyclic ABA [8]. As expected, the (−) enantiomer of the bicyclic ABA analog [8] was less effective than the corresponding (+) enantiomer. It was only active at concentrations of ≥1 µM. A similar pattern was observed for the (−) enantiomer of ABA [1], which was only effective at concentrations≥3.33 µM.

*Arabidopsis thaliana* (Columbia wild type) seed germination inhibition studies were performed as described by Cutler et. al. (23). The treatments were performed in duplicate with 50 seeds per plate and incubated at 24° C. with 16 hr days and 8 hr nights for the duration of the test (7 days).

Determining Absolute Stereochemistry of Bicyclic ABA

Figure 5:
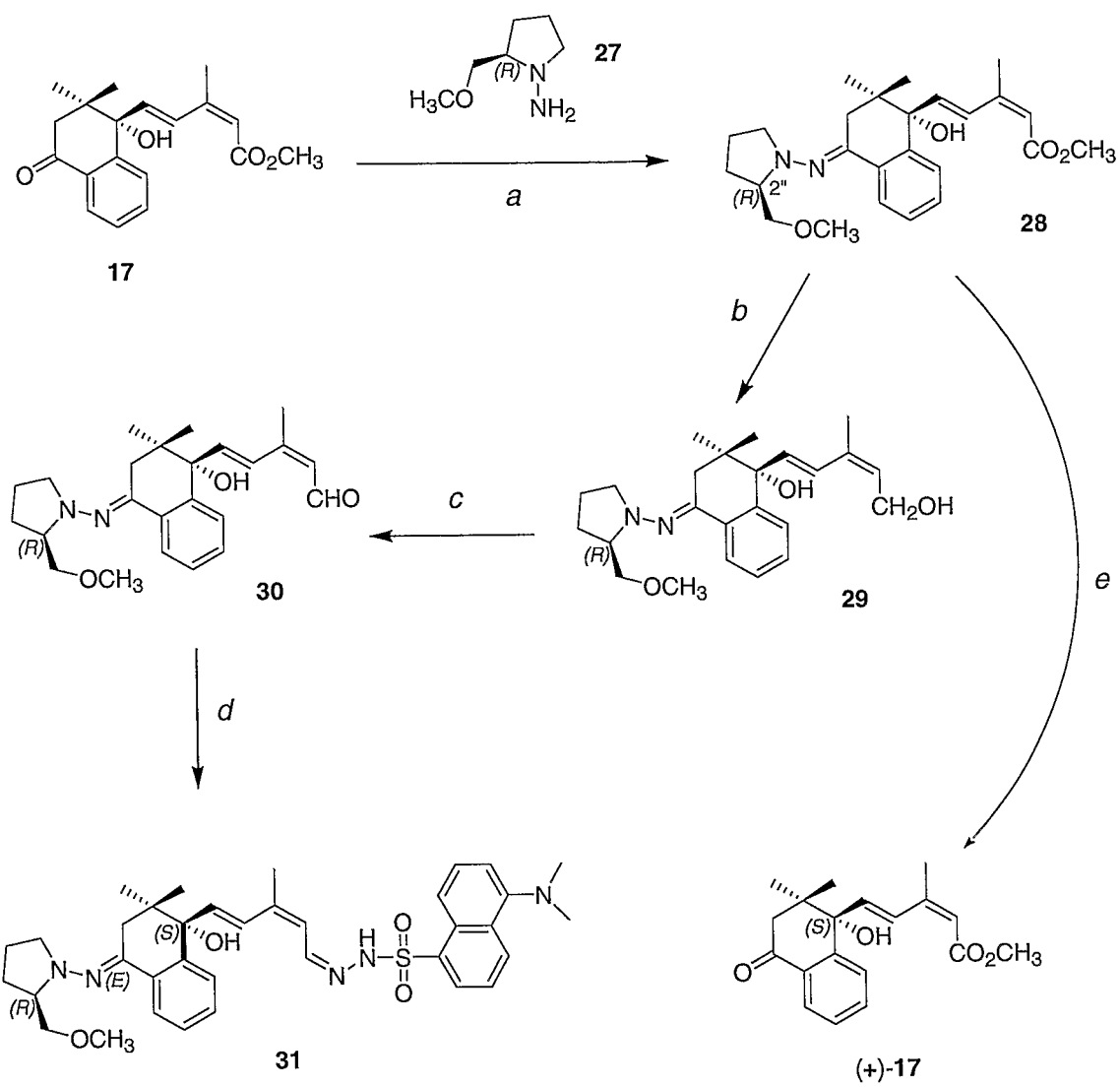
FIG. 5 is an illustration of the steps used to determine the stereochemistry of the (+)-8 bicyclic ABA shown as Compound [8] in FIG. 2. a) PTSA; b) LiAlH; c) $MnO_2$; d) $CCl_3CO_2H$/dansyl hydrazine; e) Oxalic acid.

The stereochemistry at C-1' of (+)-bicyclic ABA, was established by x-ray crystallography of a bicyclic ABA derivative (see FIG. 5), which was synthesized from the bicyclic ABA [17] (FIG. 5). The condensation of racemic [17] with commercially available (R)-1-amino-2-methoxymethylpyrrolidine (RAMP) [27] in the presence of para-toluenesulphonic acid (PTSA) gave a mixture of two diastereomers of the hydrazone [28], which were separable by column chromatography. One of the diastereomers was characterized as follows. Reduction of the ester group, followed by allylic oxidation of the resulting alcohol [29], afforded the aldehyde [30]. Condensation of the aldehyde [30] with dansyl hydrazine in the presence of trichloroacetic acid gave the derivative [31], which gave crystals suitable for x-ray analysis. As the absolute stereochemistry of one of the stereogenic centers (2"R) was known, the absolute stereochemistry at C1' was determined to be (S), as shown from the crystal structure. The hydrazone [28] was hydrolyzed in the presence of oxalic acid to afford (+)-[17], as determined by HPLC using the chiral column. The observed biological assay results for the bicyclic analog (+)-[8] are consistent with the biological activity in similar assays observed for natural (+)-ABA which also has the C1' (S) absolute stereochemistry. The laboratory steps followed are provided below.

The production of 5-[1-Hydroxy-4-(2-methoxymethyl-pyrrolidin-1-ylimino)-2,2-dimethyl-1,2,3,4-tetrahydro-naphthalen-1-yl]-3-methyl-penta-2,4-dienoic acid methyl ester [28]

To a mixture of ester [17] (42 mg, 0.13 mmol), RAMP (20 µL, 0.14 mmol), PTSA (9.2 mg, 0.048 mmol) in dry toluene (2 mL) was heated at 110°-112° C. for 1 day. The reaction mixture was diluted with $CH_2Cl_2$ after it was cooled to RT. The organic layer was washed with saturated $NaHCO_3$, dried, and evaporated to give a residue. The residue was separated by flash column chromatography (10-40µ silica gel was used with 20% ethyl acetate-hexane) to provide hydrazone 28 (22.2 mg, 40%), $[\alpha]_D$−424.8 (c 1.31, $CH_2Cl_2$) and an inseparable mixture of starting material and the other diastereomeric product (25.3 mg).

FTIR (λ max): 3457, 3060, 2965, 1714, 1634, 1448, 1381, 1158, 766 $cm^{-1}$.

$^1$H NMR ($CDCl_3$): δ 0.88 (s, 3H, 9' or 10'-$CH_3$), 0.99 (s, 3H, 10' or 9'-$CH_3$), 1.71 (m, 1H, H-3"), 1.85 (m, 2H, H-4"), 2.00 (s, 3H, 6-$CH_3$), 2.03 (m, 1H, H-3"), 2.51 (q, 1H, J=8.5 Hz, H-5"), 2.68 (q, 2H, J=16.0 Hz, H-3'), 3.29 (m, 1H, H-2"), 3.32 (s, 3H, $OCH_3$), 3.35 (m, 1H, H-5"), 3.50 (m, 2H, $CH_2OCH_3$), 5.69 (s, 1H, H-2), 6.31 (d, 1H, J=16.0 Hz, H-5), 7.23 (m, 3H, Ar—H), 7.96 (d, 1H, J=16.0 Hz, H-4), 8.11 (m, 1H, Ar—H). $^{13}$C NMR ($CDCl_3$): δ 166.6, 154.9, 150.0, 140.3, 139.7, 132.4, 129.4, 127.9, 127.8, 127.2, 124.8, 117.2, 77.7, 75.6, 67.0, 59.2, 54.6, 51.1, 39.1, 38.6, 26.8, 24.2, 24.0, 22.9, 21.3.

The Hydrolysis of Hydrazone [28].

A mixture of RAMP-hydrazone [28] (12.0 mg, 0.028 mmol) in hexane (2 mL) and $CH_2Cl_2$ (0.1 mL) saturated oxalic acid (0.5 mL) was stirred at RT for 3 days. The reaction mixture was extracted with $CH_2Cl_2$, washed with saturated $NaHCO_3$, dried and evaporated to give a residue. The residue was purified by flash column chromatography (25% ethyl acetate-hexane) to afford a product which from $^1$H NMR and the retention time from chiral HPLC (Chiralpak AS column, 250×10 mm, Diacel Chemical Industries Ltd, Japan) was confirmed as the ester (+)-17 (5.3 mg, 61%), $[\alpha]_D$+254.9 (c 0.53, $CHCl_3$).

The production of 1-(5-Hydroxy-3-methyl-penta-1,3-dienyl)-4-(2-methoxymethyl-pyrrolidin-1-ylimino)-2,2-dimethyl-1,2,3,4-tetrahydro-naphthalen-1-ol [29]

To a suspension of $LiAlH_4$ (63.7 mg, 1.68 mmol) in anhydrous ether (15 mL) was added hydrazone [28] (113 mg, 0.28 mmol) at RT and the mixture stirred at RT for 3 hr. The reaction was quenched with a drop of water and more water added. The mixture was acidified with 3N HCl to pH 4.0 and EtOAc added. The mixture was then stirred for 20 min and extracted with EtOAc, dried, and concentrated to give a crude product which was purified by column chromatography on silica gel, using 30% ethyl acetate-hexane followed by 50% ethyl acetate-hexane) to provide the pure hydrazone alcohol [29] (86.9 mg, 78%).

FTIR λ max 3418, 2965, 2871, 1448, 1384, 1099, 991, 765, 736 cm$^{-1}$.

$^1$H NMR (CDCl$_3$): δ 0.88 (s, 3H, 9' or 10'-CH$_3$), 0.97 (s, 3H, 10' or 9'-CH$_3$), 1.72 (m, 1H, H-3"), 1.86 (s, 3H, 6-CH$_3$), 1.86 (m, 2H, H-4"), 2.03 (m, 1H, H-3"), 2.51 (m, 1H, H-5"), 2.67 (q, 2H, J=8.0 Hz, H-3'), 3.29 (m, 1H, H-2"), 3.31 (s, 3H, OCH$_3$), 3.35 (m, 1H, H-5"), 3.52 (m, 2H, CH$_2$OCH$_3$), 4.17 (m, 2H, H-1), 5.56 (t, 1H, J=7.0 Hz, H-2), 5.96 (d, 1H, J=15.5 Hz, H-5), 6.83 (d, 1H, J=15.5 Hz, H-4), 7.25 (m, 3H, Ar—H), 8.11 (m, 1H, Ar—H). $^{13}$C NMR (CDCl$_3$): δ 155.1, 140.7, 134.4, 133.5, 132.5, 129.3, 128.4, 127.8, 127.1, 126.8, 124.8, 77.8, 75.6, 66.9, 59.2, 58.4, 54.6, 39.2, 38.4, 26.8, 24.2, 24.0, 22.9, 20.8.

HRMS (m/z) C$_{24}$H$_{35}$N$_2$O$_3$ requires: 399.2647 [M+1]$^+$; found: 399.2656.

The production of 5-[1-Hydroxy-4-(2-methoxymethyl-pyrrolidin-1-ylimino)-2,2-dimethyl-1,2,3,4-tetrahydro-naphthalen-1-yl]-3-methyl-penta-2,4-dienal [30]

A mixture of hydrazone alcohol [29] (69 mg, 0.17 mmol) and MnO$_2$ (300.8 mg, 3.46 mmol) in acetone (5 mL) was stirred at RT for 16 hr. The reaction mixture was filtered over a bed of Celite® and washed with acetone. The combined filtrates and washings were evaporated to give a residue, which was purified by column chromatography on silica using 30% ethyl acetate-hexane to provide the hydrazone aldehyde [30] (54.4 mg, 79%) and [α]$_D$ −532.6 (c 0.43, CH$_2$Cl$_2$).

FTIR (λ max): 3429, 3060, 2965, 2873, 1666, 1632, 1120, 766, 736 cm$^{-1}$.

1H NMR (CDCl$_3$): δ 0.94 (s, 3H, 9' or 10'-CH$_3$), 1.03 (s, 3H, 10' or 9'-CH$_3$), 1.75 (m, 1H, H-3"), 1.89 (m, 2H, H-4"), 2.07 (m, 1H, H-3"), 2.10 (s, 3H, 6-CH$_3$), 2.55 (m, 1H, H-5"), 2.71 (q, 2H, J=6.5 Hz, H-3'), 3.32 (m, 1H, H-2"), 3.34 (s, 3H, OCH$_3$), 3.40 (m, 1H, H-5"), 3.54 (m, 2H, CH$_2$OCH$_3$), 5.90 (d, 1H, J=8.0 Hz, H-2), 6.38 (d, 1H, J=15.5 Hz, H-5), 7.27 (m, 3H, Ar—H), 7.58 (d, 1H, J=15.5 Hz, H-4), 8.16 (m, 1H, Ar—H), 10.2 (d, 1H, J=8.0 Hz, H-1).

$^{13}$CNMR (CDCl$_3$): δ 190.4, 154.0, 153.6, 140.8, 139.7, 132.6, 129.5, 128.9, 128.3, 127.0, 125.7, 125.1, 78.0, 75.6, 67.0, 59.2, 54.8, 39.2, 38.7, 26.8, 24.3, 24.0, 23.0, 21.6.

HRMS (m/z) C$_{24}$H$_{33}$N$_2$O$_3$ requires: 397.2458 [M+1]; Found: 397.2490.

The Production of Dansyl Hydrazone [31].

A mixture of the hydrazone aldehyde [30] (48.9 mg, 0.12 mmol), dansyl hydrazine (32.8 mg, 0.12 mmol) and trichloroacetic acid (8.6 mg, 0.053 mmol) in ethanol (2 mL) was heated at 75° C. for 5 min. The reaction was quenched by addition of several drops of sat. NaHCO$_3$. The ethanol was removed in vacuo to give a residue, which was diluted with CH$_2$Cl$_2$ and washed with water, dried and concentrated to provide a crude product. The crude product was purified by column chromatography on silica gel (10-40μ) using 30% ethyl acetate in hexane to give the pure dansyl hydrazone [31] (62.4 mg, 79%) as a yellow powder. The yellow powder was recrystallized from hexane-ethyl acetate (4:1) to give the crystalline product: Mp: 110.1-114.9° C. (decomposition), [α]$_D$ −305.8 (c 0.38, CH$_2$Cl$_2$).

FTIR (λ max): 3513, 3214, 3059, 2960, 2871, 1689, 1610, 1574, 1453, 1334, 1164, 1146, 790, 766, 736, cm$^{-1}$.

$^1$H NMR (CDCl$_3$): δ 0.88 (s, 3H, 9' or 10'-CH$_3$), 0.95 (s, 3H, 10' or 9'-CH$_3$), 1.70 (m, 1H, H-3"), 1.88 (s, 3H, 6-CH$_3$), 1.88 (m, 2H, H-4"), 2.02 (m, 1H, H-3"), 2.54 (m, 1H, H-5'), 3.16 (m, 2H, H-3'), 2.86 (s, 6H, N(CH$_3$)$_2$), 3.32 (s, 3H, OCH$_3$), 3.32 (m, 1H, H-2"), 3.38 (m, 1H, H-5"), 3.52 (m, 2H, CH$_2$OCH$_3$), 5.93 (d, 1H, J=10.0 Hz, H-2), 6.04 (d, 1H, J=15.0 Hz, H-5), 6.86 (d, 1H, J=15.0 Hz, H-4), 7.15 (d, 1H, J=7.5 Hz, Ar—H), 7.25 (m, 3H, Ar—H), 7.53 (m, 2H, Ar—H), 7.91 (d, 1H, J=10.0 Hz, H-1), 8.12 (m, 1H, Ar—H), 8.24 (s, br, 1H, NM), 8.35 (m, 2H, Ar—H), 8.54 (d, 1H, J=7.5 Hz, Ar—H).

$^{13}$CNMR (CDCl$_3$): δ 154.4, 151.9, 145.0, 141.0, 140.3, 136.1, 133.6, 132.5, 131.1, 131.1, 129.8, 129.8, 129.4, 128.4, 128.1, 127.0, 126.2, 124.8, 124.4, 123.3, 118.9, 115.2, 78.0, 75.6, 66.7, 59.0, 54.8, 45.4, 39.2, 38.6, 26.7, 24.2, 24.0, 22.9, 21.0.

HRMS (m/z) C$_{36}$H$_{46}$N$_5$O$_4$S requires: 644.3270 [M+1]; Found: 644.3265.

Bicyclic ABA was recrystallized from methanol at RT and the absolute configurations determined by x-ray crystallography. Data was collected at −100° C. on a Nonius Kappa CCD diffractometer, using the COLLECT program (26). Cell refinement and data reductions used the programs DENZO and SCALEPACK (27). SIR97 (24) was used to solve the structure and SHELXL97 (30) was used to refine the structure. XTAL3.7 (25) was used for molecular graphics. H atoms were placed in calculated positions with U$_{iso}$ constrained to be 1.2 times U$_{eq}$ of the carrier atom for methine, methylene and aromatic protons and 1.5 times U$_{eq}$ of the carrier atoms for methyl, N—H and O—H hydrogen atoms. The data were as follows:

Crystal data and structure refinement for (+)-8

| | | |
|---|---|---|
| Empirical formula | C$_{38}$H$_{53}$N$_5$O$_6$S | |
| Formula weight | 707.91 | |
| Temperature | 173(2) K | |
| Wavelength | 0.71073 Å | |
| Crystal system | Orthorhombic | |
| Space group | P 2$_1$2$_1$2$_1$ | |
| Unit cell dimensions | a = 11.2340(2) Å | α = 90°. |
| | b = 16.3940(2) Å | β = 90°. |
| | c = 20.9930(3) Å | γ = 90°. |
| Volume | 3866.28(10) Å$^3$ | |
| Z | 4 | |
| Density (calculated) | 1.216 Mg/m$^3$ | |
| Absorption coefficient | 0.134 mm$^{-1}$ | |
| F(000) | 1520 | |
| Crystal size | 0.20 × 0.15 × 0.13 mm$^3$ | |
| Theta range for data collection | 3.43 to 27.48°. | |
| Index ranges | −14 <= h <= 14, | |
| | −20 <= k <= 21, | |
| | −27 <= l <= 27 | |
| Reflections collected | 32824 | |
| Independent reflections | 4913 [R (int) = 0.0637] | |
| Completeness to theta = 27.48° | 99.7% | |
| Absorption correction | None | |
| Refinement method | Full-matrix least-squares on F$^2$ | |
| Data/restraints/parameters | 4913/0/462 | |
| Goodness-of-fit on F$^2$ | 1.033 | |
| Final R indices [I > 2sigma(I)] | R1 = 0.0420, wR2 = 0.0932 | |
| R indices (all data) | R1 = 0.0541, wR2 = 0.0992 | |
| Absolute structure parameter | 0.39(9) | |
| Largest diff. peak and hole | 0.460 and −0.372 e · Å$^{-3}$ | |

REFERENCES

1. Finkelstein R. R., Gampala S. S. L. and Rock C. D., *Plant Cell,* 14, S15-S45, (2002)

2. Finkelstein R. R. and Rock C. D. *The Arabidopsis Book.* Editors C. R. Somerville and E. M. Meyerowitz. American Society of Plant Biologists, Rockville Md., USA. DOI/ 10.1199/tab.0058, available at www.aspb.orgipublications/ arabidopsis/(2002)

3. Walton D. C., Abscisic acid, F. T. Addicott (ed). Praeger, N.Y., p 113, (1983). b. Hite D. C. R., Outlaw W. H. and Seavy M. A., *Physiol. Plant,* 92, 79 (1994); c. Walker-Simmons, M. K., P. A. Rose, A. C. Shaw and S. R. Abrams. 1994. Plant Physiol. 106: 1279-1284. d. Churchill, G. C., B. Ewan, M. J. T. Reaney, L. V. Gusta and S. R. Abrams. 1992. Plant Physiology 100: 2024-2029. e. Perras, M., P. Rose, E. W. Pass, K. B. Chatson, J. J. Balsevich and S. R. Abrams. 1997. Phytochemistry 46: 215-222. f. Nakano, S., Todoroki, Y., Hirai, N., Ohigashi, H. 1995 Biosci. Biotech. Biochem. 59: 1699-1706.

4. Abrams S. R., Rose P. A., Cutler P. A., Balsevich J. J., Lei B. and Walker-Simmons M. K., *Plant Physiol.,* 114, 89 (1997). b. Rose P. A., Cutler A. I., Irvine N. M., Shaw A. C., Squires T. M., Loewen M. K. and Abrams S. R., *Bio. Med. Chem. Lett.,* 7, 2543 (1997).

5. Cutler A. J. and Krochko J. E., *Trends Plant Sci.,* 4, 472 (1999).

6. Balsevich J. J., Cutler A. J., Lamb N., Friesen L. J., Kurz E., Perras M. R. and Abrams S. R., *Plant Physiol.,* 106, 135 (1994).

7. Hampson C. R., Reaney M. J. T., Abrams G. D., Abrams S. R. and Gusta L. V., *Phytochemistry,* 31, 2645 (1992).

8. Zhou, R., S. J. Ambrose, M. M. Galka, A. J. Cutler, T. M. Squires, M. K. Loewen, K. Nelson, A. Jadhav, D. C. Taylor and S. R. Abrams. 2004 Plant Physiology 361-369.

9. Krochko J. E., Abrams G. D., Loewen M. K. Abrams S. R. and Cutler J. A., *Plant Physiol.,* 118, 849 (1998); Qi, Q., P. A. Rose, G. D. Abrams, D. C. Taylor, S. R. Abrams and A. J. Cutler. 1998. Plant Physiology. 117: 979-987.

10. Irvine N. M., Rose P. A., Cutler A. J., Squires T. M. and Abrams S. R., *Phytochemistry,* 53, 349 (2000).

11. Yamazaki, D., Yoshida S., Asami, T., and Kuchitsu, K., 2003 Plant Journal 35 129-139.

12. Bergmann F. and Hirshberg Y., *J. Amer. Chem. Soc.,* 65, 1429 (1943).

13. Dorman G. and Prestwich G. D., *Biochemistry,* 33, 5661 (1994).

14. Hornberg C. and Weiler E. W., *Nature,* 310, 321 (1984).

15. Cornelussen M. H. M., Karssen C. M. and van Loon L. C., *Phytochemistry,* 39, 959 (1995).

16. Coumbarides G. S., Eames J. and Weerasooriya N., *Label. Compd. Radiopharm.,* 45, 917 (2002).

17. Chidambaram N. and Chandrasekaran S., *J. Org. Chem.,* 52, 5048 (1987).

18. Perras M., Rose P. A., Pass E. W., Chatson B., Balsevich J. J. and Abrams S. R., *Phytochemistry,* 46, 215 (1997).

19. Churchill G. C., Reaney M. J. T., Abrams S. R. and Gusta L. V., *Plant Growth Regulation,* 25, 35 (1998).

20. Walker-Simmons M. K., Reaney M. J. T., Quarrie S. A., Perata P., Vernieri P. and Abrams S. R., *Plant Physiol.,* 95, 46 (1991).

21. Kohler A. D., Beale M. H., Rollason R., Barratt D. H., Lewis M. J., Van der Meulen R. M. and Wang M., *J. Chem. Soc., Perkin Trans.* 1, 1543 (1997); Pedron J., Braut M., Nake C. and Miginiac E., *Eur. J. Biochem.,* 252, 385 (1998).

22. Ludwig S. R., Sommers D. A., Peterson W. L., Pohlmann B. F., Zarovitz M. A., Gengenbach B. G. and Messing J., *Theor. Appl. Genet.,* 71, 344 (1985).

23. Cutler A. J. Rose P. A., Squires T. M., Loewen M. K., Shaw A. C., Quail J. W., Krochko J. E. and Abrams S. R., *Biochemistry,* 39, 13614 (2000).

24. Altomare A., Burla, M. C., Camalli M., Cascarano G., Giacovazzo C., Guagliardi A., Moliterni A. G. G., Polidori G. and Spagna R., *J. Appl. Cryst.,* 32, 115 (1999).

25. Hall S. R., du Boulay D. J. and Oltlof-Hazekamp R., (ed). Xtal3.7 System. University of Western Australia (2000).

26. Nonius. COLLECT. Nonius BV, Delft, The Netherlands (1998)

27. Ontwinowski Z. and Minor W., *Methods in Enzymology,* 276, *Macromolecular Crystallography,* Part A, Carter C. W. and Sweet R. M. (ed), pp. 307-326. London: Academic Press (1997).

28. Sheldrick G. M., SBELXL97. University of Göttingen. Germany (1997).

What is claimed is:

1. A compound having the following structural formula:

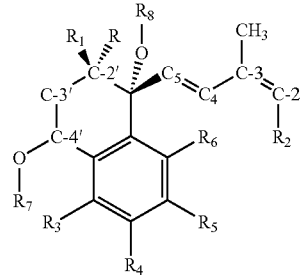

wherein, R and $R_1$ are independently X, XOH, or XOX, where X is alkyl, alkenyl, alkynyl;

wherein, $R_2$ is $CH_2OH$, CHO, COOH or COOX;

wherein R3 through R6 are independently H, OH, X, XOH, XOX, OX, halogen, Ohalogen, XOhalogen, or Xhalogen;

wherein, $R_7$ is H, X, an additional bond to C-4' to create a carbonyl, or XO cyclized with C-4'; and wherein, Rs is H or methyl.

2. The compound of claim 1 wherein, R and/or $R_1$ is a vinyl group, allyl group, acetylene group, or methyl acetylene.

3. The compound of claim 1 wherein, $R_2$ and C-4 are in a cis conformation.

4. A method of effectively treating a plant to affect a physiological process of a plant, the method comprising, contacting the plant with an effective amount of the compound of claim 1.

5. The method of claim 4 wherein the physiological process of the plant is reducing plant cell growth, the method comprising contacting the plant with an effective amount of the compound of claim 1.

6. The method of claim 4 wherein the physiological process of the plant is reducing seed germination, the method comprising contacting the plant with an effective amount of the compound of claim 1.

7. The method of claim 4 wherein the physiological process of the plant is controlling plant seed germination, the method comprising contacting the plant with an effective amount of the compound of claim 1.

8. The method of claim 4 wherein the physiological process of the plant is enhancing antitranspirant activity in a plant, the method comprising contacting the plant with an effective amount of the compound of claim 1.

9. The method of claim 4 wherein the physiological process of the plant is enhancing ABA-induced gene expression in a plant, the method comprising contacting the plant with an effective amount of the compound of claim 1.

10. The method of claim 4 wherein the physiological process of the plant is reducing transplantation shock in a plant seedling, the method comprising contacting the plant with an effective amount of the compound of claim 1.

11. The method of claim 4 wherein the physiological process of the plant is promoting root growth in a plant, the method comprising contacting the plant with an effective amount of the compound of claim 1.

12. The method of claim 4 wherein the physiological process of the plant is increasing root-shoot ratio in a plant, the method comprising contacting the plant with an effective amount of the compound of claim 1.

13. The method of claim 4 wherein the physiological process of the plant is increasing survival potential in a plant, the method comprising contacting the plant with an effective amount of the compound of claim 1.

14. The method of claim 4 wherein the physiological process of the plant is the enablement of fall seeding of spring crops, the method comprising contacting the plant with an effective amount of the compound of claim 1.

15. The method of claim 7 wherein the plant is a weed.

16. The method of claim 4 wherein the physiological process of the plant is the production of seed products, the method comprising contacting the plant with an effective amount of the compound of claim 1.

17. The method of claim 16, wherein the production of seed products is for micropropagaton.

18. The method of claim 4, wherein the compound is selected from the group consisting of: acetylene bicyclic ABA, 5-(1-Hydroxy-2-methyl-4-oxo-2-vinyl-1,2,3,4-tetrahydro-naphthalen-1-yl)-3-methyl-penta-2,4-dienoic acid methyl ester, (2Z,4EJ-5-[(1'S,2'SJ-1'-Hydroxy-2'-hydroxymethyl-2'-methyl-4'-oxo-1',2',3',4'-tetrahydronaphthalen-1'-yl]-3-methylpenta-2,4-d ienoic acid, 5-(1-Hydroxy-2-methyl-4-oxo-2-vinyl-1,2,3,4-tetrahydro-naphthalen-1-yl)-3-methyl-penta-2,4-dienoic acid methyl ester, 1-tetralone; 2,2-dimethyl-1-tetralone; (2Z)(1R)-1-(5-Hydroxy-3-methyl-pent-3-en-1-ynyl)-2,2-dimethyl-1,2,3,4-tetrahydro-naphthalen-1-ol; (1'E,3'ZJ-1-(5'Hydroxy-3'-methylpenta-1',3'-dienyl)-2,2-dimethyl-1,2,3,4-tetrahydronaphthalen-1-ol; Methyl-(2Z,4E)-5-((1S)-1-Hydroxy-2,2-dimethyl-1,2,3,4-tetrahydro-naphthalen-1-yl)-3-methyl-penta-2,4-dienoate; 5-(1-Hydroxy-2,2-dimethyl-1,2,3,4,-tetrahydro-naphthalen-1-yl)-3-methyl-Pent-2-en-4-ynoic acid methyl ester, 2-Methyl-1-naphthol, 2-Methyl-4,4-ethylenedioxynaphthalen-1-one; (3ZJ-1-(5'-Hydroxy-3'-methylpent-3'-en-1'-ynyl-4-oxo-2-methyl-1,4-dihydronaphthalen-1-ol ethane-1,2-diyl ketal; 1-(5-hydroxy-3-methyl-penta-1,3-dienyl)-2-methyl-4,4-ethylened ioxynaphthalen-1-ol; Methyl (2Z,4EJ-5-(1'-hydroxy-2'-methyl-4'-oxo-1',4'-dihydronaphthalen-1'-yl)-3-methylpenta-2,4-dienoate ethane-1,2-diyl ketal; 5-(1-Hydroxy-2-methyl-4-oxo-1,4-dihydro-naphthalen-1-yl)-3-methyl-penta-2,4-dienoic acid methyl ester, and any combination thereof.

19. The compound of claim 1 wherein the compound has the following formula: (+)-(2Z,4E)-5-((1'S)-1'-Hydroxy-2',2'-dimethyl-4'-oxo-1',2',3',4'-tetrahydronaphthalen-1 '-yl)-3-methylpenta-2,4-dienoic acid.

20. The compound of claim 1 wherein the compound has the following formula: (2Z,4E)-Methyl 5-((1'S,2'R)-1'-hydroxy-2'-methyl-4'-oxo-2'vinyl-1',2',3',4'-tetrahydronaphthalen-1'-yl)-3-methylpenta-2,4-dienoate.

21. The compound of claim 1 wherein the compound has the following formula: (2Z,4E)-Methyl 5-((1'S)-1'-hydroxy-2',2'-dimethyl-4'-oxo-1',2',3',4'-tetrahydronaphthalen-1'-yl)-3-methylpenta-2,4-dienoate.

* * * * *